United States Patent
Quay

(10) Patent No.: US 6,703,513 B1
(45) Date of Patent: Mar. 9, 2004

(54) PRODUCTION AND USE OF DERIVATIZED HOMOSERINE LACTONES

(75) Inventor: Steven C. Quay, Edmonds, WA (US)

(73) Assignee: K-Quay Enterprises LLC, Edmonds, WA (US)

( * ) Notice: Subject to any disclaimer, the term of this patent is extended or adjusted under 35 U.S.C. 154(b) by 0 days.

(21) Appl. No.: 09/587,116

(22) Filed: Jun. 2, 2000

(51) Int. Cl.⁷ .............................................. C07D 317/08
(52) U.S. Cl. ....................... 549/229; 549/230
(58) Field of Search ................. 549/229, 230

(56) References Cited

U.S. PATENT DOCUMENTS

| | | | |
|---|---|---|---|
| 5,591,872 A | 1/1997 | Pearson et al. | 549/321 |
| 5,593,827 A | 1/1997 | Bycroft et al. | 435/6 |
| 5,821,077 A | 10/1998 | Salmond et al. | 435/41 |

FOREIGN PATENT DOCUMENTS

| | | | | |
|---|---|---|---|---|
| WO | 96/16079 | * | 5/1996 | |
| WO | WO 96/29392 | | 9/1996 | C12N/1/20 |

OTHER PUBLICATIONS

Schineller, et al, Arch. Microbiol., 1986, 146(1), 35–40.*
Davies, et al., "The involvement of cell-to-cell signals in the development of a bacterial biofilm," *Science*, 280:295–298 (Apr. 10, 1998).
Fuqua, et al., "Quorum sensing in bacteria: the LuxR–LuxI family of cell density-responsive transcriptional regulators," *J. Bacteriology*, 176(2):269–275 (Jan. 1994).

* cited by examiner

*Primary Examiner*—Joseph K. McKane
*Assistant Examiner*—Andrea D. Small
(74) *Attorney, Agent, or Firm*—Townsend and Townsend and Crew LLP

(57) ABSTRACT

The present invention provides analogues of autoinducer molecules that are derivatized to allow their attachment to other molecules and surfaces. Libraries of the autoinducer analogues are also contemplated. Also provided are methods for using the compounds of the invention to produce compositions, such as immunoconjugates, antibodies and vaccines, which are useful for treating and preventing disease states in a subject. The compositions of the invention are also useful in various assays, including assessing the autoinducer load in a subject.

23 Claims, 3 Drawing Sheets

Scheme I[†]

[†] a. Ac$_2$O, reflux
b. C$_6$H$_5$CH$_2$OH/CH$_2$Cl$_2$
c. homoserine lactone hydrobromide, EDC, HCl, CH$_2$Cl$_2$, pyridine
d. Pd/C, H$_2$, EtOAc

PRODUCTION AND USE OF DERIVATIZED HOMOSERINE LACTONES

BACKGROUND OF THE INVENTION

Autoinducers ("AIs") are extracellular signal compounds used by a variety of bacteria to regulate cellular functions in response to changes in population density. For example, light production by the marine symbiotic bacterium *Vibrio fischeri* is controlled in a population density-responsive manner by the self-produced, membrane-permeable autoinducer, N-3-oxohexanoyl-L-homoserine lactone (N-3-oxohexanoyl-L-HSL; AI-1). AI-1 accumulates in a population density-dependent manner during bacterial growth. When it reaches a threshold concentration, AI-1, via the autoinducer receptor and transcriptional activator, LuxR, activates transcription of the lux operon, luxICDABEG, which encodes autoinducer synthase (luxI) and luminescence enzymes. (Eberhard et al., *Biochemistry* 20: 2444–2449 (1981); Engebrecht et al. Cell, 32: 773–781 (1983); Engebrecht et al., *Proc. Natl. Acad. Sci. USA* 81: 4154–4158 (1984); Hanzelka et al., *J. Bacteriol.* 177: 815–817 (1995); Shadel et al.,*J. Bacteriol.* 172: 3980–3987 (1990); Slock et al., *J. Bacteriol.*, 172:3974–3979 (1990); Swartzman et al.,*J. Bacteriol.* 172: 6797–6802 (1990)). The autoinduction mechanism in *V. fischeri* also involves, among other regulatory aspects, an AI-1 mediated luxR negative autoregulation (Dunlap et al., *J. Bacteriol.* 170: 4040–4046 (1988); Dunlap et al., *J. Bacterial.* 171: 3546–3552 (1989); Engebrecht et al., *Genet. Eng.* 8: 31–44 (1986); Shadel et al., *J. Bacteriol.* 173: 568–574 (1991); Shadel et al., *J. Biol. Chem.* 267: 7690–7695 (1992)).

Long thought to be a regulatory mechanism unique to the luminescence system of *V. fischeri* and certain closely related marine luminous bacteria, autoinduction of gene expression recently has been identified in a wide variety of other bacteria (Fuqua et al., *J. Bacteriol.* 176:269–275 (1994)). The diversity of species using autoinduction and the chemical and genetic similarities of their autoinduction systems indicate that autoinduction is an evolutionary conserved regulatory mechanism commonly used by bacteria to sense and respond to population density.

All bacteria presently known to utilize AIs associate with higher organisms, i.e., plants and animals, at some point during their lifecycles. For example, *Pseudomonas aeruginosa* is an opportunistic pathogen in humans with cystic fibrosis. P. aerugitiosa regulates various virulence determinants with AI (Davies et al. Science 280: 295 (1998)). Other examples of AI producing bacteria include *Erwinia carotovora, Pseudomonas aureofaciens, Yersinia enterocolitica, Vibrio harveyi,* and *Agrobacterium tumefaciens*. *E. carotovora* infects certain plants and creates enzymes that degrade the plant's cell walls, resulting in what is called "soft rot disease." *E. carotovora* produces the autoinducer N-3-oxohexanoyl-L-HSL. *Yersinia enterocolitica* is a bacterium, which causes gastrointestinal disease in humans and has been reported to produce an autoinducer. *P. aureofaciens* associates with the roots of plants and produces antibiotics that block fungus growth in the roots. That antibiotic synthesis is under autoinducer control.

In addition to the known naturally occurring autoinducers, recent work has focused on the synthesis and testing of synthetic analogues of certain autoinducers. For example, Bycroft et al., U.S. Pat. No. 5,593,827 have synthesized a series of N-(β-ketocaproyl)-L-homoserine lactone derivatives. The homoserine lactone derivatives are active autoinducers and control gene expression in certain organisms. Additionally, the autoinducer analogue N-(3-oxododecanoyl)-homoserine lactone has been shown to inhibit the activity of *P. aeruginosa* (Pearson et al., U.S. Pat. No. 5,591,872). Furthermore, autoinducer analogues based on a furanone ring structure have been shown to inhibit homoserine lactone regulated processes in microorganisms (Kjellberg et al., WO 96/29392). Cao and coworkers have synthesized a series of N-acyl homoserine lactones and assessed their binding parameters and structure-function relationship in the *V. harveyi* lux system. None of these references describes the synthesis of autoinducer analogues that are suitable for attachment to other molecules and surfaces.

Autoinducer molecules are thought to have particular relevance in the progression of cystic fibrosis (CF). CF is the most common inheritable lethal disease among Caucasians. There are approximately 25,000 CF patients in the U.S.A. The frequency of CF in several other countries (e.g., Canada, United Kingdom, Denmark) is high (ranging from 1 in 400 to 1 in 1,600 live births).

Chronic respiratory infections caused by mucoid *Pseudomonas aeruginosa* are the leading cause of high morbidity and mortality in CF. The initially colonizing *P. aeruginosa* strains are nonmucoid but in the CF lung they inevitably convert into the mucoid form. The mucoid coating composed of the exopolysaccharide alginate leads to the inability of patients to clear the infection, even under aggressive antibiotic therapies. The emergence of the mucoid form of *P. aeruginosa* is associated with further disease deterioration and poor prognosis.

The microcolony mode of growth of *P. aeruginosa*, embedded in exopolysaccharide biofilms in the lungs of CF patients (Lam et al., *Infect. Immun.* 28: 546 (1980)), among other functions, plays a role in hindering effective opsonization and phagocytosis of *P. aeruginosa* cells (Pier et al., *N. Engl. J. Med.* 317: 793–8 (1987); Pier et al., Infect Immun. 60: 4768–76 (1992)). Although CF patients can produce opsonic antibodies against *P. aeruginosa* antigens, in most cases phagocytic cells cannot effectively interact with such opsonins (Pressler et al., *Clin. Exp. Immunol.* 90: 209–14 (1992); Pier et al., *Science* 249: 537–40 (1990)). Physical hindrance caused by the exopolysaccharide alginate and a functionally important receptor-opsonin mismatch caused by chronic inflaztnation and proteolysis are contributing factors to the ineffective interactions (Tosi et al., *J. Infect. Dis.* 162: 156–62 (1990)). Moreover, the biofilm prevents the effective delivery of exogenous antimicrobial agents to the microorganisms of the colony (de Beer et al., *Appl. Environ. Microbiol.* 60: 4339 (1994)).

Compounds and compositions facilitating the study of autoinduction mechanisms, particularly biofilm formation, arid which are effective in disrupting biofilms or retarding their formation would represent a significant advance in the treatment of disease states associated with biofilms, such as CF. Quite surprisingly, the present invention provides such compounds and compositions.

SUMMARY OF THE INVENTION

Thus, in a first aspect, the present invention provides a compound having a structure according to Formula I:

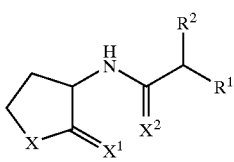
(I)

wherein, $R^1$ is preferably a member selected from —H, —OH, and (═O); $R^2$ is preferably a member selected from reactive functional groups, alkyl groups terminally substituted with a reactive functional group and internally substituted alkyl groups terminally substituted with a reactive functional group; X is preferably a member selected from —O—, —S— and —NH—; and $X^1$ and $X^2$ are preferably members independently selected from O and S.

In a second aspect, the present invention provides a compound having the structure according to Formula II:

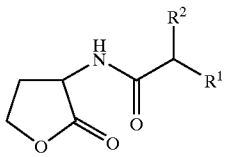
(II)

wherein, $R^1$ is preferably a member selected from H, OH, and (═O), and $R^2$ is preferably a member selected from reactive functional groups, alkyl groups terminally substituted with a reactive functional group and internally substituted alkyl groups terminally substituted with a reactive functional group.

In a third aspect, the present invention provides a compound having a structure that is a member selected from:

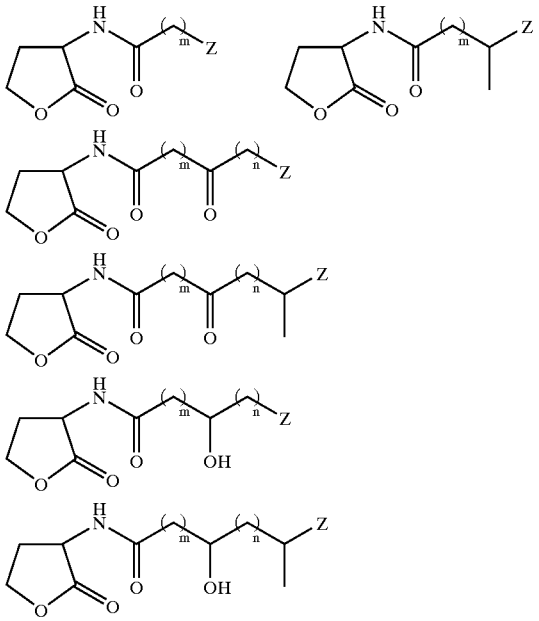

wherein, m is preferably a number selected from 1 to 20, inclusive; n is preferably a number from 0 to 20, inclusive; and Z is a reactive functional group.

In a fourth aspect, the invention provides an immobilized compound comprising a solid support to which is attached a molecule comprising a structure according to Formula VI:

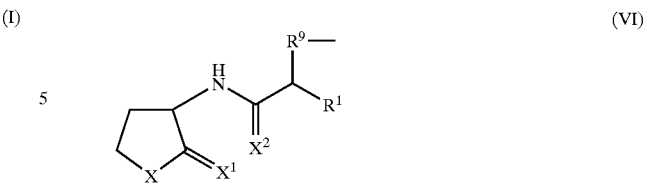
(VI)

wherein, $R^1$ is preferably a member selected from —H, —OH, and (═O); $R^9$ is preferably a member selected from alkyl groups and substituted alkyl groups and is attached to a solid support, X is preferably a member selected from —O—, —S— and —NH—; and $X^1$ and $X^2$ are preferably members independently selected from O and S.

In a fifth aspect the present invention provides an immunogenic conjugate comprising a target component including a structure according to Formula VI, above, wherein $R^9$ is attached to a carrier molecule.

In a sixth aspect, the invention provides a library of compounds having a structure according to Formula I, wherein the library comprises a first compound according to Formula I and a second compound according to Formula I, wherein the first compound differs from the second compound in the identity of a member selected from $R^1$, $R^9$, X, $X^1$, $X^2$ and combinations thereof.

In a seventh aspect, the invention provides a kit for detecting an autoinducer in a sample. The kit includes, an antibody that binds specifically to the autoinducer and directions for using the antibody to detect the autoinducer.

In a eighth aspect, the invention provides a method of detecting an autoinducer in a sample. The method includes, the steps of (a) contacting the sample with an antibody that specifically binds to the autoinducer; and (b) determining whether the sample contains the autoinducer.

In an ninth aspect, the present invention provides a method of monitoring the amount of autoinducer in a patient treated with an agent that inhibits the growth of an organism producing the autoinducer. The method includes: (a) providing a sample from the patient treated with the growth inhibiting agent; (b) contacting the sample with an antibody that specifically binds to an autoinducer; (c) forming a complex between the antibody and the autoinducer; and (d) determining the amount of autoinducer in the patient sample by detecting the antibody or the antibody-autoinducer complex and comparing the amount of antibody detected in the patient sample to a standard curve, thereby monitoring the amount of autoinducer in the patient.

In a tenth aspect, the invention provides a method of isolating an autoinducer. The method includes the steps of: (a) providing a sample comprising the autoinducer; (b) contacting the sample with an antibody that specifically binds to the autoinducer, thereby forming an antibody-autoinducer complex; and (c) isolating the autoinducer by isolating the antibody-autoinducer complex.

In a eleventh aspect, the invention provides a method of detecting an antibody that specifically binds to an autoinducer. The method include the steps of: (a) providing a sample; (b) contacting the sample with a peptide that specifically binds to the antibody; and (c) detecting the antibody.

DETAILED DESCRIPTION OF THE INVENTION AND THE PREFERRED EMBODIMENTS

Introduction

Figure 1:
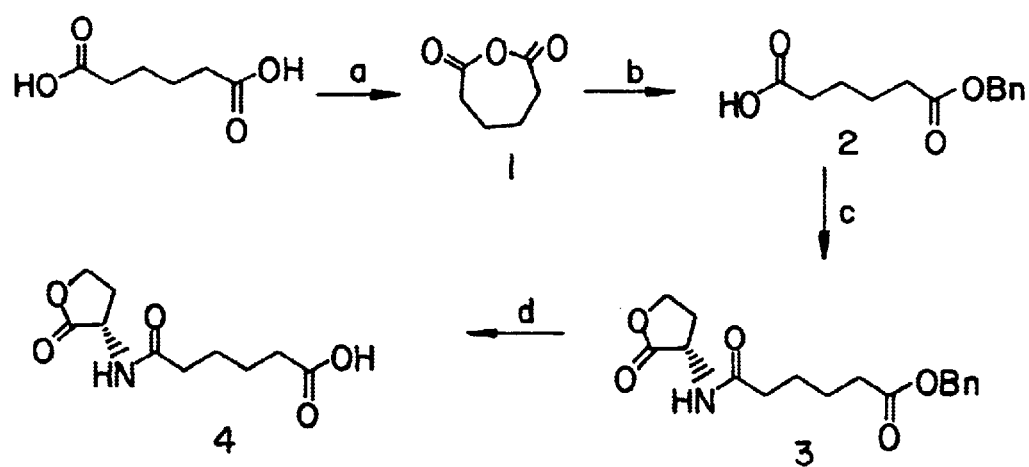
FIG. 1 is an exemplary synthetic scheme for the preparation of compound 4.

The present invention provides, for the first time, an array of autoinducer analogues that are derivatized with a reactive group that allows the conjugation of the analogues to surfaces and to other molecules. The reactive autoinducer analogues are useful for the preparation of materials such as affinity chromatography supports, immunogenic conjugates, autoinducer libraries, and the like. The immobilized or conjugated autoinducers are used for, among other things, raising mono- and poly-clonal antibodies against autoinducers, isolating cellular receptors that interact with autoinducers and detecting molecules (e.g., antibodies) that interact with autoinducers. The efficacy of art-recognized anti-infective agents can be increased by conjugating them to the reactive autoinducer analogues described herein. The reactive autoinducer analogues are easily synthesized, often from commercially available precursors. Moreover, as the fields of bioconjugate chemistry, peptide synthesis and oligonucleotide synthesis provide a wealth of techniques for coupling small reactive molecules to surfaces, polymers, (e.g., biomolecules), and to other small molecules, the ready availability of autoinducers derivatized to allow their conjugation to other species provides access to a wealth of compounds and compositions of diagnostic and therapeutic use, as well as compounds useful in elucidating the structure and mechanism of action of autoinducers.

Definitions

The terms used to describe the preferred embodiments of the present invention will generally have their art-recognized meanings. The definitions offered below are intended to supplement, not supplant, the art-recognized meanings.

"RAA," as used herein refers to "reactive autoinducer analogue."

The term "independently selected" is used herein to indicate that the groups so described can be identical or different "Autoinducer," as used herein includes molecules that are preferably a component of a system that regulates intercellular activity in response to environmental conditions and includes extracellular signal molecules. Exemplary autoinducers include, for example, the acylated homoserine lactones of microorganisms, such as *Vibrio harveyi* and *P. aeruginosa* and an array of structurally analogous compounds. The term "autoinducer" is a generic term that also incorporates, for many purposes, the term "autoinducer analogue" and includes the reactive autoinducer analogues of the invention.

"Autoinducer analogue," is generally used herein to refer to a species of the invention. The compounds of the invention are preferably structurally analogous to known autoinducer molecules, with the exception that the molecules of the invention include within their structure a reactive functional group that allows them to be tethered to other molecules and/or surfaces. "Autoinducer analogues" also encompasses, the compounds of the invention that have been tethered to another molecule or surface via reaction of their reactive functional group.

The terms "isolated," "purified," or "biologically pure" refer to material that is substantially or essentially free from components that normally accompany it as found in its native or crude state. A material that is the predominant species present in a preparation is substantially purified. Purity and homogeneity are typically determined using analytical chemistry techniques such as polyacrylamide gel electrophoresis or high performance liquid chromatography (HPLC). When used in combination with proteins and nucleic acids, the term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoranidates, methyl phosphonates, chiral-methyl phosphonates, 2-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605–2608 (1985): Rossolini et al., *Mol. Cell. Probes* 8: 91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. These terms also encompass the term "antibody."

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γcarboxyglutamate, and O-phosphoserine. Amino acid analogs refers to compounds that have the same basic chemical structure as a naturally occurring amino acid, i.e. an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "immunoassay" refers to an assay that uses an antibody to specifically bind an antigen. The immunoassay is characterized by, for example, the use of specific binding properties of a particular antibody to isolate, target, and/or quantify the antigen.

The phrase "specifically (or selectively) binds" to an antibody or "specifically (or selectively) immunoreactive with," when referring to an autoinducer or other substance (e.g., protein, peptide), delineates a binding reaction that is determinative of the presence of the autoinducer in a heterogeneous population of the autoinducer and other substances, preferably biologics. Thus, under designated immunoassay conditions, the specified antibodies bind to a particular autoinducer or autoinducer analogue. The antibody preferably does not substantially bind in a significant amount to other substances present in the sample. Specific binding to an antibody under such conditions may require an antibody that is selected for its specificity for a particular autoinducer. For example, polyclonal antibodies raised to an autoinducer can be selected to obtain only those polyclonal antibodies that are specifically immunoreactive with the autoinducer and not with other autoinducers or other substances. This selection can be achieved by subtracting out antibodies that cross-react with molecules such as other autoinducers.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo. A "host cell" also refers to a cell, such as a hybridoma, that produces an antibody.

"Biological sample." as used herein, includes a sample of biological tissue or fluid that contains an autoinducer or an anti-autoinducer antibody. Such samples include, but are not limited to, tissue isolated from humans. Fluids include blood, serum, plasma, urine, sputum, cerebral spinal fluid, and other such fluids. Biological samples may also include sections of tissues such as frozen sections taken for histologic purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

The term "alkyl" includes branched or unbranched, saturated or unsaturated, monovalent hydrocarbon radical, generally having from about 1–30 carbons and preferably, from 4–20 carbons and more preferably from 6–18 carbons. When the alkyl group has from 1–6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyl."

"Substituted alkyl" includes alkyl as just described including one or more substituents such as lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

The term "aryl" is used herein includes an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "substituted aryl."

"Substituted aryl" includes aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "arylalkyl" is used herein to refer to a subset of "aryl" in which the aryl group is attached to another group by an alkyl group as defined herein.

"Substituted arylalkyl" defines a subset of "substituted aryl" wherein the substituted aryl group is attached to another group by an alkyl group as defined herein.

The term "acyl" is used to describe a ketone substituent, —C(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used to describe primary amines, —NRR', wherein R and R' are independently H, alkyl, aryl or substituted analogues thereof. "Amino" encompasses "alkylamino" denoting secondary and tertiary amines and "acylamino" describing the group RC(O)NR'.

The term "alkoxy" is used herein to refer to the —OR group, where R is alkyl aryl, or substituted analogues thereof. Suitable alkoxy radicals include, for example, methoxy, ethoxy, t-butoxy, etc.

The term "acyloxy" is used interchangeably with "ester" to describe an organic radical derived from an organic acid by the removal of the acidic hydrogen. Simple acyloxy groups include, for example, acetoxy, and higher homologues derived from carboxylic acids such as ethanoic, propanoic, butanoic, etc. The acyloxy moiety may be oriented as either a forward or reverse ester (i.e. RC(O)OR' or R'OC(O)R), wherein one or both of R and R' is a component of the parent molecule having the "acyloxy" group as a substituent.

As used herein, the term "aryloxy" denotes aromatic groups, which are linked to another group directly through an oxygen atom. Exemplary aryloxy groups include phenoxy, substituted phenoxy, benzyloxy, phenethyloxy. "Aryloxy" encompasses "substituted aryloxy" moieties in which the aromatic group is substituted as described above for "substituted aryl."

As used herein "aryloxyalkyl" defines aromatic groups attached, through an oxygen atom to an alkyl group, as defined herein. The term "aryloxyalkyl" encompasses "substituted aryloxyalkyl" moieties in which the aromatic group is substituted as described for "substituted aryl."

As used herein, the term "mercapto" defines moieties of the general structure R—S—R' wherein R and R' are the same or different and one or more or R and R' is a component of the parent molecule having the mercapto group as a substituent.

The term "saturated cyclic hydrocarbon" denotes carbocyclic groups such as, for example, cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a non-aromatic carbocycle with at least one double bond, such as, for example, cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are replaced by a heteroatom such as nitrogen, oxygen or sulfur. Heteroaryl refers to structures, which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to the parent molecule.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiohiophene, pyridine, isoxazole, phthalimide, pyrzole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to the parent molecule.

The term "heterocyclic" is used herein to describe a monovalent saturated or unsaturated non-aromatic group having a single ring or multiple condensed rings from 1–12 carbon atoms and from 14 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to another group.

The Compounds

In a first aspect, the present invention provides a molecule having a structure according to Formula I:

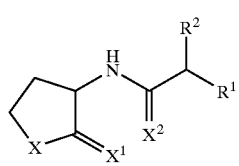

(I)

$R^1$ is preferably a member selected from —H, —OH, and (=O); $R^2$ is preferably a member selected from H, reactive functional groups, alkyl groups terminally substituted with a reactive functional group and internally substituted alkyl groups terminally substituted with a reactive functional group; X is preferably a member selected from —O—, —S— and —NH—; and $X^1$ and $X^2$ are preferably members independently selected from O and S. In another embodiment, $X^1$ is preferably an amine derivative such as an alkyl-, or hydroxyl-amine. In yet another embodiment, X is preferably an alkyl-, acyl-, or hydroxyl-amine.

In a second aspect, the present invention provides compounds having a structure according to Formula II:

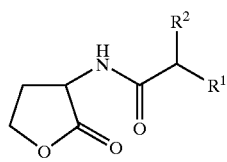

(II)

$R^1$ is preferably a member selected from H, OH, and (=O); and $R^2$ is preferably a member selected from reactive functional groups, alkyl groups terminally substituted with a reactive functional group and internally substituted alkyl groups terminally substituted with a reactive functional group.

The following discussion is generally applicable to each of the aspects of the invention discussed above. In a preferred embodiment, $R^2$ is an internally substituted alkyl group terminally substituted with a reactive functional group. The alkyl group can be straight- or branched-chain and it can include regions of unsaturation. The internally substituted alkyl group can be functionalized at with substituents that interrupt the alkyl chain, with substituents pendent from the alkyl chain or a combination thereof. Substantially any type of substituent and/or substitution pattern, which can be incorporated into an alkyl group is useful in practicing the present invention. Furthermore, the alkyl chain described herein is not limited in the number or identity of the substitutions that it bears. Those of skill in the art are able to select appropriate substitutions for a particular application. Useful internal substitutions include, for example, —O—, —NR—, —S—, double bonds (e.g. C=C, C=N, C=O) and the like. Preferred substituents pendent from the alkyl chain include, for example, —OH, —NRR', —NRR'R"⁺, —SH, —COOR and the like. As used herein, R, R' and R" represent H, unsubstituted and substituted alkyl and aryl groups. Presently preferred internal substituents include OH, (=O) and combinations thereof.

In preferred embodiments of each of the above-described aspects of the present invention, the alkyl and the internally substituted alkyl groups are members selected from $C_1$–$C_{20}$ saturated straight-chain, $C_1$–$C_{20}$ saturated branched-chain, $C_1$–$C_{20}$ unsaturated straight-chain, $C_1$–$C_{20}$ unsaturated branched-chain alkyl and internally substituted alkyl groups, and more preferably, the $C_5$–$C_{10}$ analogues of each of the above-recited structures.

In still further preferred embodiments, $R^2$ has the structure set forth in Formula III:

$$—(CH_2)_n—R^7 \qquad \text{(III)}$$

wherein, $R^7$ is a reactive functional group; and n is a number from 1 to 20, inclusive, and more preferably, a number from 2 to 9, inclusive.

In yet another preferred embodiment, R² has a structure according to Formula IV:

(IV)

wherein, R⁷ is a reactive functional group, and q and s are numbers independently selected from 1 to 20, inclusive, more preferably, from 2 to 9, inclusive In a third aspect, the present invention provides compounds having a structure according to the structures displayed in Table 1.

TABLE 1

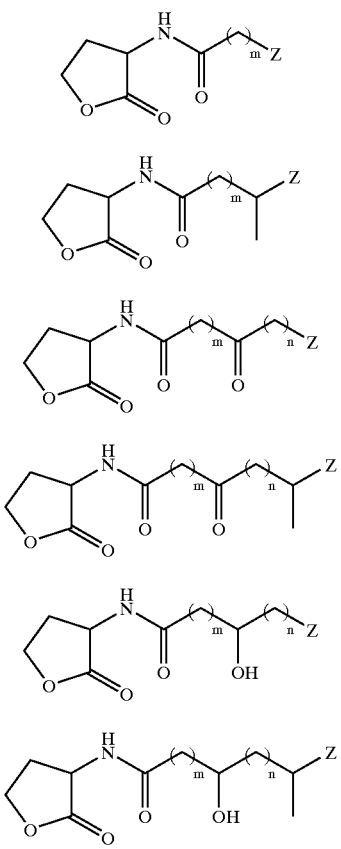

In each of the compounds displayed in Table 1, Z represents a reactive functional group and m and n are preferably numbers independently selected from 1 to 20, inclusive, more preferably from 2 to 9, inclusive.

The compounds of the invention can be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds are prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S Encyclopedia of Practical Organic Chemistry 5th ED., Longman Scientific and Technical Ltd., Essex, 1991, pp. 809–816; and Heller, Acc. Chem. Res. 23: 128(1990).

Reactive Functional Groups

The compounds of the invention bear a reactive functional group, which can be located at any position on the alkyl chain, but which is generally located at a terminal position of the molecule. Reactive groups and classes of reactions useful in practicing the present invention are generally those that are well known in the art of bioconjugate chemistry. Currently favored classes of reactions available with reactive autoinducer analogues are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Useful reactive functional groups include, for example:

(a) carboxyl groups and various derivatives thereof including, but not limited to, N-hydroxysuccinimide esters, N-hydroxybenztriazole esters, acid halides, acyl imidazoles, thioesters, pnitraphenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkylithium addition;

(f) sulfonyl halide groups for subsequent reaction with amines, for example, to form sulfonamides;

(g) thiol groups, which can be converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive autoinducer analogue. Alternatively, a reactive functional group can be protected from participating in the reaction by the presence of a protecting group. Those of skill in the art will understand how to protect a particular functional group from interfering with a chosen set of reaction conditions. For examples of useful protecting groups, See Greene et al., Protective Groups in Organic Synthesis, John Wiley & Sons, New York, 1991.

In a preferred embodiment, the reactive functional group is selected from the groups —OR$^3$, —NHR$^4$, —COR$^5$, —SH and —CH$_2$X$^3$ In these groups, —OR$^3$ is selected from hydroxyl, alkyl sulfonate or aryl sulfonate groups. R$^4$ is selected from H, C$_1$–C$_6$ alkyl, C$_1$–C$_6$ substituted alkyl, aryl and substituted aryl groups. R$_5$ is selected from H, X$^3$ and —OR$^6$. R$^6$ is a species selected such that —OR$^6$ is a leaving group. X$^3$ is a halogen.

In a further preferred embodiment R$^6$ is selected from alkyl, substituted alkyl, aryl, substituted aryl, heteroaryl, substituted heteroaryl, heterocyclyl and substituted heterocyclyl groups.

In a still further preferred embodiment, R$^3$ has a structure according to Formula V:

wherein, R$^8$ is a member selected from alkyl, substituted alkyl. aryl and substituted aryl groups.

In yet another preferred embodiment, the reactive functional group is selected from —COOH, OH, —NH$_2$, and —SH.

Synthesis

The compounds of the invention are synthesized by an appropriate combination of generally well known synthetic methods. Methods of synthesizing the compounds of the invention are both readily apparent and accessible to those of skill in the relevant art. The discussion below is offered to illustrate certain of the diverse methods available for use in assembling the compounds of the invention, it is not intended to define the scope of reactions or reaction sequences that are useful in preparing the compounds of the present invention.

One method of synthesizing compounds of the invention is set forth in Scheme 1 (FIG. 1). A precursor dicarboxylic acid is activated at a single carboxylic acid by conversion of the dicarboxylic acid to the corresponding cyclic anhydride 1. The cyclic anhydride is subsequently reacted with benzyl alcohol. The reaction of the cyclic anhydride with benzyl alcohol provides a dicarboxylic acid derivative 2 in which only one of the carboxylic acid moieties is protected. The unprotected carboxylic acid group is coupled to the exocyclic amine group of homoserine lactone using a dehydrating reagent in a modification of art-recognized peptide chemistry to produce lactone derivative 3. The benzyl alcohol moiety is removed by hydrogenolysis using a Pd/C catalyst to afford acid 4.

Figure 2:
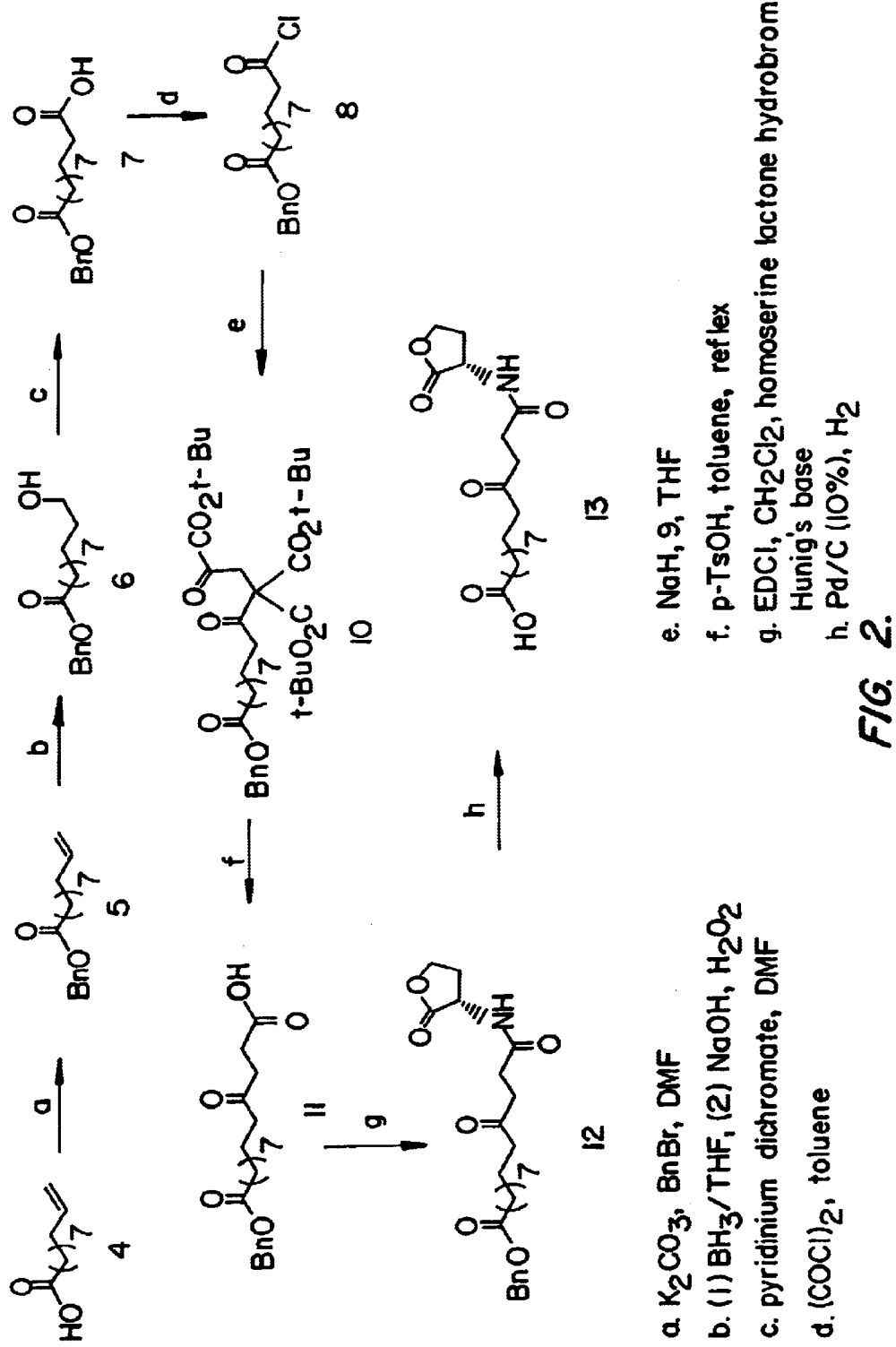
FIG. 2 is an exemplary synthetic scheme for the preparation of compound 13.
Figure 3:
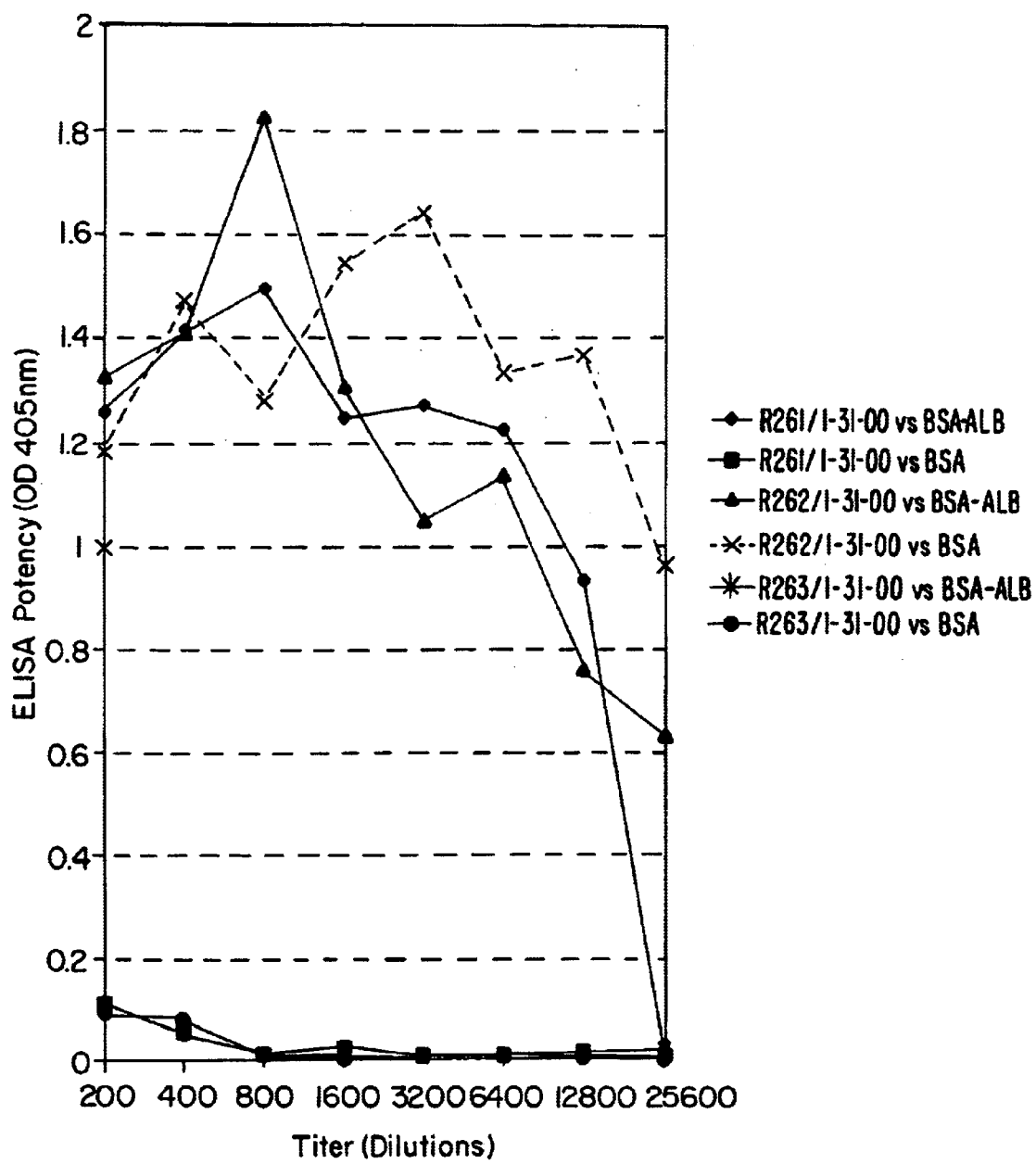
FIG. 3 is a graphical display of the ELISA results vs. dilution for antibodies of the invention.

Another method for synthesizing compounds of the invention is set forth in FIG. 2 (Scheme 2). An alkenyl carboxylic acid 4 is protected by benzylation, forming 5. The alkene group of the protected acid is hydroborated and oxidized, affording alcohol 6. The alcohol is further oxidized to the corresponding carboxylic acid 7, which is subsequently activated by conversion to an acyl chloride 8. The acyl chloride is reacted with a compound capable of providing a carbon atom chain of a desired length and which also includes a carboxylic acid or a precursor thereof 10.

Decarboxylation of 10 affords a monoprotected dioic acid 11. The monoprotected acid is coupled to the exocyclic amine of homoserine lactone to provide compound 12, which is debenzylated, affording 13.

A number of variations on the basic schemes set forth above are useful in synthesizing the compounds of the invention. For example, the synthesis of certain compounds of the invention requires a dicarboxylic acid having a carbon backbone that is either too long or too short to produce useful yields of a cyclized anhydride. Dicarboxylic acids that cannot be cyclized, can be monoprotected. Numerous methods allowing the monoprotection of a dicarboxylic acid are known in the art. In one exemplary method, a single carboxylic acid moiety is reacted at the expense of the other acid (see, for example, Albert et al., Synthesis 635 (1987)). In another method, both of the carboxylic acid groups are protected as esters and a reagent that predominantly cleaves one ester is utilized to form the monoprotected adduct. Exemplary cleaving reagents include, but are not limited to, barium hydroxide (Inoue et al., Tetrahedron Lett. 4063 (1977)) and esterases (Ohno et al., Tetrahedron 40:145 (1984)). Many other means of monoprotecting a homodifunctional molecule are known in the art. For example, see, generally, Greene et al., Protective Groups in Organic Synthesis 2$_{ND}$ ED., Wiley-Interscience, 1991.

Following the monoprotection of the dicarboxylic acid, the remaining carboxylic acid moiety is coupled to the exocyclic amine of the heterocyclic portion of the molecule. Numerous reagents and carboxylic acid derivatives are useful in activating the carboxylic acid moiety for reaction with the amine. Carboxylic acids can be activated by conversion to, for example, acyl halides, acid anhydrides, esters (e.g., methyl) and active esters (e.g., N-hydroxysuccinimide). For example, see, generally, Sandler et al., Organic Functional Group Preparations 2$^{ND}$ ED., Chapter 11, Academic Press, Inc., Dan Diego, 1983.

The cyclic portion of the molecule can be obtained from commercial sources (e.g., Aldrich, Sigma, Fluka). For example, both homocysteine thiolactone hydrochloride and homoserine lactone hydrobromide are commercially available (Aldrich). Alternatively, appropriate five-member heterocycles can be prepared by methods known in the art (see, generally, March, Advanced Organic Chemistry 3$^{RD}$ ED., Wiley-Interscience, New York, 1985 and Katritzky, Handbook of Heterocyclic Chemistry, Pergamon Press Ltd., Oxford, 1985 ). The preparation of five-member heterocyclic ring systems is a well developed field of endeavor. The techniques necessary to prepare an array of five-member heterocyclic systems useful in preparing the compounds of the present invention are known to and easily practiced by those of skill in the art of organic synthesis.

An appropriately functionalized five-member cyclic lactam can be prepared by, for example, cyclizing an amino acid, such as 2,4-diaminobutyric acid (see, e.g., Bladé-Font, Tetrahedron Lett. 21: 2443 (1980). Many other methods, including cyclizing halo amides, hydrocarboxylation of unsaturated amines and reaction between cyclic ketones an hydrazoic acid can be used to prepare useful lactam derivatives.

The lactones, thiolactones and lactams of the invention can be converted to derivatives in which the carbonyl oxygen is replaced with a sulfur or amine group using methods known in the art. For example, the carbonyl oxygen of lactones, thiolactones and lactamns can be replaced by a sulfur atom using a reagent, such as bis(tricyclohexyltin) sulfide and BCl$_3$ (see, for example, Pederson et al., Bull. Soc. Chim. Belges 87: 229 (1978); Pederson et al., Bull. Soc. Chim. Belges 87: 293 (1978); and Ghattas et al. Sulfur Lett. 1: 69 (1982)).

It will be apparent to those of skill in the art that useful synthetic schemes can diverge from those set forth in Schemes 1 and 2 in a number of ways. In one example, a heterobifunctional compound having a single carboxylic acid moiety and a non-carboxylic acid moiety can be incorporated into the structure of the compounds of the invention. For example, a compound such as an ω-amino acid can be protected at the amine position and utilized in an otherwise unchanged method according to Schemes 1 and 2. Following assembly of the desired molecule and deprotection of the amine group, the product bears a reactive amine functionality, which allows for its attachment to another molecule or structure. Similar schemes utilizing carboxylic acids with, for example. ω-hydroxyl, -thiol, -disulfide, -carbonyl, -diene, -dienophile, and the like can be readily practiced. Furthermore, it will be apparent to those of skill in the art that the non-carboxylic acid group need not be at the ω and can be located at other positions on the chain.

Conjugated Autoinducer Analogs

In another preferred embodiment, the present invention provides an immobilized compound comprising a molecule, or a solid support to which is attached a molecule comprising a structure according to Formula VI:

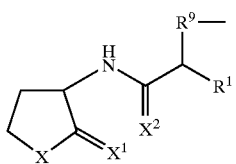

(VI).

In Formula VI, $R^1$ is preferably a member selected from —H, —OH, and (=O). $R^9$ is preferably a member selected from alkyl groups and substituted alkyl groups. X is preferably a member selected from —O—, —S— and —NH—. $X^1$ and $X^2$ are preferably members independently selected from O and S. In another preferred embodiment, $X^1$ is an amine derivative such as an alkyl-, or hydroxyl-amine. In yet another embodiment, X is an alkyl-, acyl-, or hydroxyl-amine.

In the interest of clarity, the discussion below focuses on the attachment of autoinducer molecules to solid supports. It will be apparent to those of skill in the art that this discussion also encompasses embodiments of the invention in which the autoinducer is attached to a species other than a solid support, such as a soluble or an insoluble molecule.

The compound of the invention can be immobilized on substantially any polymer, biomolecule, and solid or semi-solid material having any useful configuration. When the support is a solid or semi-solid, preferred solid supports include beads, particles, membranes, substantially planar surfaces and combinations thereof formulated from materials including silica, metal, plastic and combinations thereof According to the present invention, the surface of a solid support is functionalized with a compound of the invention (RAA) by reacting a RAA with a reactive group on the surface of the solid support, thereby derivatizing the solid support with one or more autoinducer analogues. Reactive groups which can be used in practicing the present invention are discussed in detail above and include, for example, amines, hydroxyl groups, carboxylic acids, carboxylic acid derivatives, alkenes, sulfhydryls, siloxanes. etc.

A large number of solid supports appropriate for practicing the present invention are available commercially. Useful commercially available solid supports include, for example, peptide synthesis resins, both with and without attached amino acids and/or peptides (e.g., alkoxybenzyl alcohol resin, aminomethyl resin, aminopolystyrene resin, benzhydrylamine resin, etc. (Bachem)), functionalized controlled pore glass (BioSearch Technologies), ion exchange media (Aldrich), functionalized membranes (e.g., —COOH membranes, Ashai Chemical Co., Asahi Glass Co., and Tokuyama Soda Co.), and the like.

Moreover, for applications in which an appropriate solid support is not commercially available, a wide variety of reaction types is available for the functionalization of a solid support surface. For example, supports constructed of a plastic such as polypropylene, can be surface derivatized by chromic acid oxidation, and subsequently converted to hydroxylated or aminomethylated surfaces. The functionalized support is then reacted with a RAA of complementary reactivity such as a RAA active ester, acid chloride or sulfonate ester, for example. Supports made from highly crosslinked divinylbenzene can be surface derivatized by chloromethylation and subsequent functional group manipulation. Additionally, functionalized substrates can be made from etched, reduced polytetrafluoroethylene When the support is constructed of a siliceous material such as glass, the surface can be derivatized by reacting the surface Si—OH, SiO—H, and/or Si—Si groups with a functionalizing reagent.

In a preferred embodiment, wherein the substrates are made from glass, the covalent bonding of the reactive group to the glass surface is preferably achieved by conversion of groups on the substrate's surface by a silicon modifying reagent such as:

(VII)

where $R^a$ is preferably an alkyl group, such as methyl or ethyl, $R^b$ is a linking group between silicon and $X^a$, and $X^a$ is a reactive group or a protected reactive group.

In another preferred embodiment, the reagent used to functionalize the solid support provides for more than one reactive group per each reagent molecule. Using reagents, such as VIII, below, each reactive site on the substrate surface is, in essence, "amplified" to two or more functional groups:

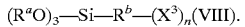(VIII).

where $R^a$ is preferably an alkyl group (e.g., methyl, ethyl), $R^b$ is a linking group between silicon and $X^a$, $X^a$ is a reactive group or a protected reactive group and n is preferably an integer between 2 and 50, and more preferably between 2 and 20. Silane derivatives having halogens or other leaving groups beside the displayed alkoxy groups of VII and VIII are also useful in the present invention.

The amplification of an autoinducer by its attachment to a silicon-containing substrate is intended to be exemplary of the general concept of autoinducer amplification. This amplification strategy is equally applicable to other aspects of the invention in which an autoinducer analogue is attached to another molecule or solid support.

A number of siloxane functionalizing reagents can be used, for example:

1. Hydroxyalkyl siloxanes (Silylate surface, functionalize with diborane, and $H_2O_2$ to oxidize to the alcohol)
   a. allyl tichlorosilane→→3-hydroxypropyl
   b. 7-oct-1-enyl trichlorchlorosilane→→8-hydroxyoctyl
2. Diol(dihydroxyalkyl)siloxanes (silylate surface and hydrolyze to diol)
   a. (glycidyl trimethoxysilane→→(2,3-dihydroxypropyloxy)propyl 3. Aminoalkyl siloxanes (amines requiring no intermediate functionalizing step)
   a. 3-aminopropyl trimethoxysilane aminopropyl
4. Dimeric secondary amninoalkyl siloxanes
   a. bis(3-trinetboxysilylpropyl)amine→bis(silyloxylpropyl)amine.

It will be apparent to those of skill in the art that an array of similarly useful functionalizing chemistries are available when support components other than siloxanes are used. Thus, for example alkyl thiols, functionalized as discussed above in the context of siloxane-modifying reagents, can be attached to metal films and subsequently reacted with an RAA to produce the immobilized compound of the invention.

R groups of use for $R^b$ in the above described embodiments of the present invention include, but are not limited to, alkyl, substituted alkyl, aryl, arylalkyl, substituted aryl, substituted arylalkyl, acyl, halogen, hydroxy, amino, alkylamino, acylamino, alkoxy, acyloxy, aryloxy, aryloxyalkyl, mercapto, saturated cyclic hydrocarbon, unsaturated cyclic hydrocarbon, hetcroaryl, heteroarylalkyl, substituted heteroaryl, substituted heteroarylalkyl, heterocyclic, substituted heterocyclic and heterocyclicalkyl groups and combinations thereof.

The immobilized constructs of the invention can also include a spacer moiety between the reactive group of the solid support and the autoinducer analogue. The properties of the linker between the solid support and the solid support reactive group and the linker between the solid support reactive group and the autoinducer analogue have structures and chemical compositions that are independently selected from a large array of stable and cleavable structures. For the purpose of illustration, the discussion below focuses on the linker between the solid support and the solid support reactive group. The discussion is also generally relevant to a linker, if present, between the solid support reactive group and the autoinducer analogue.

In Formulae VII and VIII, above, $R^b$ is either stable or it can be cleaved by chemical or photochemical reactions. For example, $R^b$ groups comprising ester or disulfide bonds can be cleaved by hydrolysis and reduction, respectively. Also within the scope of the present invention is the use of $R^b$ groups, which are cleaved by light such as, for example, nitrobenzyl derivatives, phenacyl groups, benzoin esters, etc. Other such cleaveable groups are well-known to those of skill in the art.

In a preferred embodiment, the immobilized construct includes a spacer between the solid support reactive group and the autoinducer analogue. The linker is preferably selected from $C_6$–$C_{30}$ alkyl groups, $C_6$–$C_{30}$ substituted alkyl groups, polyols, polyethers (e.g., poly(ethyleneglycol)), polyamines, polyamino acids, polysaccharides and combinations thereof.

In those embodiments in which the spacer moiety includes a cleavable moiety, that moiety is preferably selected from groups that are cleaved by light, heat, oxidation, reduction, enzymatic action, hydrolysis and combinations thereof, and are more preferably selected from disulfides and esters.

Immunogenic Conjugates

Also provided by the present invention are immunogenic conjugates having a structure including a target region according to Formula IX:

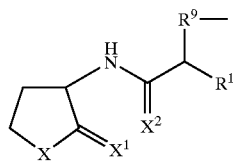

(IX).

In which, $R^1$ is preferably a member selected from —H, —OH, and (=O). $R^9$ is preferably a member selected from alkyl groups and substituted alkyl groups. X is a member selected from —O—, —S— and —NH—. $X^1$ and $X^2$ are preferably members independently selected from O, S and NH. $R^9$ is attached to a carrier that renders the autoinducer analogue immunogenic or enhances the immunogenicity of the autoinducer analogue, such as a protein or adjuvant.

As used herein "target region" refers to that portion of the immunoconjugate which an immune system component, such as an antibody, T cell, or the like, will recognize or interact with. It is understood that the entire target region or only a portion thereof may interact with an immune system component.

Commonly used carriers are large molecules that are highly immunogenic and capable of imparting their immunogenicity to a hapten coupled to the carrier. Examples of carriers include, but are not limited to, proteins, lipid bilayers (e.g., liposomes), synthetic or natural polymers (e.g., dextran, agarose, poly-L-lysine) or synthetic organic molecules. Preferred immunogenic carriers are those that are immunogenic, have accessible functional groups for conjugation with a hapten, are reasonably water-soluble after derivatization with a hapten, and are substantially non-toxic in vivo. Although any carrier capable of enhancing the immunogenicity of compounds according to Formula IX, are useful in the present invention, presently preferred carriers include, for example protein carriers having a molecular weight of greater than or equal to 5000 daltons, more preferably, albumin or hemocyanin.

The immunogenicity of the autoinducer compositions of the present invention may further be enhanced by linking the autoinducer analogue to one or more peptide sequences that are able to a elicit a cellular immune response (see, e.g., WO 94/20127). Peptides that stimulate cytotoxic T lymphocyte (CTL) responses as well as peptides that stimulate helper T lymphocyte (HTL) responses are useful for linkage to the compounds of the invention. The peptides can be linked by a spacer molecule. The spacer is typically comprised of relatively small, neutral molecules, such as amino acids or amino acid mimetics, which are uncharged under physiological conditions.

A compound of the invention may be linked to a T helper peptide that is recognized by T helper cells in the majority of the population. This can be accomplished by selecting amino acid sequences that bind to many, most, or all of the HLA class II molecules. An example of such a T helper peptide is tetanus toxoid at positions 830–843 (see, e.g., Panina-Bordignon et al., *Eur. J. Immunol.* 19: 2237–2242 (1989)).

Further, a compound of the invention may be linked to multiple antigenic determinants to enhance immunogenicity. For example, in order to elicit recognition by T cells of multiple HLA types, a synthetic peptide encoding multiple overlapping T cell antigenic determinants (cluster peptides) may be used to enhance immunogenicity (see, e.g., Ahlers et al., *J. Immunol.* 150: 5647–5665 (1993)). Such cluster peptides contain overlapping, but distinct antigenic determinants. The cluster peptide may be synthesized colinearly with a peptide of the invention. The cluster peptide may be linked to a compound of the invention by one or more spacer molecules.

A peptide composition comprising a compound of the invention linked to a cluster peptide may also be used in conjunction with a cluster peptide linked to a CTL-inducting epitope. Such compositions may be administered via alternate routes or using different adjuvants.

Alternatively multiple peptides encoding CTL and/or HTL epitopes may be used in conjunction with a compound of the invention.

Many methods are known to those of skill in the art for coupling a hapten to a carrier. In an exemplary embodiment, a RAA comprising a sulfhydryl group is combined with keyhole limpet hemocyanin, which has been activated by SMCC (succinimidyl-4-(N-maleimidomethyl)cyclohexane-1-carboxylate), Dewey et al., *Proc. Natl. Acad. Sci. USA* 84: 5374–5378 (1987). The sulfhydryl-bearing RAA useful in this method can be synthesized by a number of art-recognized methods. For example, a RAA bearing a terminal carboxyl group is coupled with cysteamine, using a dehydrating agent, such as dicyclohexylcarbodiimide (DCC), to form a dimeric RAA, linked via a disulfide bridge. The disulfide bridge is cleaved by reduction, affording the monomeric sulfhydryl-derivatized RAA.

In yet another preferred embodiment, $R^9$ comprises a spacer moiety situated between the target component and the carrier. The discussion above regarding the characteristics of spacer moieties located between the reactive group of the solid support and the autoinducer analogue is substantially applicable to the present embodiment. In an exemplary embodiment, the spacer arm includes a poly(ethyleneglycol) (PEG) group. Bifunctional PEG derivative appropriate for use in this method are commercially available (Shearwater Polymers) or can be prepared by methods well known in the art. In an exemplary embodiment, the SMCC activated KLH, infra, is reacted with a PEG-RAA conjugate, bearing a sulfhydryl group. An appropriate conjugate can be prepared by a number of synthetic routes accessible to those of skill in the art. For example, a commercially available product, such as t-Boc-NH-PEG-NHH$_2$, is reacted with a carboxyl terminal RAA in the presence of a dehydrating agent (e.g., DCC). thereby forming the PEG amide of the RAA. The t-Boc group is removed by acid treatment (e.g., trifluoroacetic acid, TFA), to afford the deprotected amino PEG amide of the RAA. The deprotected RAA is subsequently reacted with a sulfhydryl protected molecule, such as 3-mercaptopropionic acid or a commercially available thiol and amine protected cysteine, in the presence of a dehydrating agent. The thiol group is then deprotected and the conjugate is reacted with the SMCC activated KLH to provide an autoinducer analogue linked to a carrier via a PEG spacer group.

The exemplary embodiments presented above are intended to illustrate general reaction schemes that are useful in preparing certain of the compounds of the present invention and should not be interpreted as limiting the scope of the invention or the pathways useful to produce the compounds of the invention.

In another preferred embodiment, the immunogenic conjugate has a structure including a target region according to Formula X:

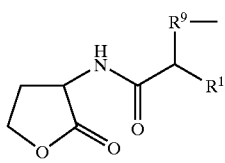

(X)

wherein, $R^1$ is preferably a member selected from H, OH, and (=O); and $R^9$ is preferably a member selected from alkyl and substituted alkyl groups.

In a further preferred embodiment, the target component has a structure including a target region according to Formula XI:

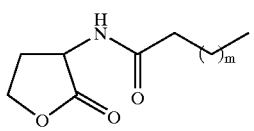

(XI)

wherein, m is preferably a number from 0 to 30, inclusive.

Antibodies

The present invention also provides antibodies that specifically bind to autoinducer structures selected from native autoinducers (e.g., N-(3-oxohexanoyl)homoserine lactone, N-(D-3-hydroxybutanoyl)homoserine lactone, etc.), autoinducer analogues (e.g., N-3hydroxyvaleryl)homoserine lactone), immobilized autoinducer analogues, reactive autoinducer analogues and immunogenic conjugates as described herein.

"Antibody" generally refers to a polypeptide comprising a framework region from an immunoglobulin or fragments thereof that specifically binds and recognizes an antigen. The recognized immunoglobulins include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially an Fab with part of the hinge region (see, Fundamental Immunology (Paul ed., 3$^{rd}$ ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain Fv).

For preparation of monoclonal or polygonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in Monoclonal Antibodies and Cancer Therapy, Alan R. Liss. Inc. (1985)).

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the tiler of reactivity to the beta subunits. When appropriately high titers of antibody to the immunogen are obtained, blood is collected from the animal and antisera are prepared. Further fractionation of the antisera to enrich for antibodies reactive to the protein can be done if desired.

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6: 511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246: 1275–1281 (1989).

Monoclonal antibodies and polyclonal sera are collected and titered against the immunogen in an immunoassay, for example, a solid phase immunoassay with the immunogen immobilized on a solid support. Typically, polygonal antisera with a titer of $10^4$ or greater are selected and tested for their cross reactivity against different autoinducers, using a competitive binding immunoassay. Specific polygonal antisera and monoclonal antibodies will usually bind with a $K_d$ of at least about 0.1 mM. more usually at least about 1 $\mu$M, preferably at least about 0.1 $\mu$M or better, and most preferably, 0.01 $\mu$M or better.

Techniques for the production of single chain antibodies (U.S. Pat. No. 4,946,778) can be adapted to produce antibodies to compounds of this invention and the unmodified native autoinducer molecules. Also, transgenic mice, or other organisms such as other mammals, may be used to express humanized antibodies. Alternatively, phage display technology can be used to identify antibodies and heteromeric Fab fragments that specifically bind to selected antigens (see, e.g. McCafferty et al., *Nature* 348: 552–554 (1990); Marks et al., *Biotechnology* 10: 779–783 (1992)).

In an exemplary embodiment, an animal, such as a rabbit or mouse is immunized with a RAA immunogenic construct as described above. The antibodies produced as a result of the immunization are preferably isolated using standard methods.

In a still further preferred embodiment, the antibody is a humanized antibody. "Humanized" refers to a non-human polypeptide sequence that has been modified to minimize immunoreactivity in humans, typically by altering the amino acid sequence to mimic existing human sequences, without substantially altering the function of the polypeptide sequence (see. e.g., Jones et al., *Nature* 321: 522–525 (1986), and published UK patent application No. 8707252).

In another preferred embodiment, the present invention provides an antibody, as described above, further comprising a member selected from detectable labels, biologically active agents and combinations thereof attached to the antibody.

When the antibody is conjugated to a detectable label, the label is preferably a member selected from the group consisting of radioactive isotopes, fluorescent agents, fluorescent agent precursors, chromophores, enzymes and combinations thereof. Methods for conjugating various groups to antibodies are well known in the art. For example, a detectable label that is frequently conjugated to an antibody is an enzyme, such as horseradish peroxidase, alkaline phosphatase, $\beta$-galactosidase, and glucose oxidase.

In an exemplary embodiment of the present invention, horseradish peroxidase is conjugated to an antibody raised against an autoinducer or autoinducer analogue. In this embodiment, the saccharide portion of the horseradish peroxidase is oxidized by periodate and subsequently coupled to the desired immunoglobin via reductive amination of the oxidized saccharide hydroxyl groups with available amine groups on the immunoglobin.

Methods of producing antibodies labeled with small molecules, for example, fluorescent agents, are well known in the art. Fluorescent labeled antibodies can be used in immunohistochemical staining (Osborn et al., *Methods Cell Biol.* 24: 97–132 (1990); in flow cytometry or cell sorting techniques (Ormrod, M. G. (ed.), Flow Cytometry. A Practical Approach, IRL Press, New York, 1990); for tracking and localization of antigens, and in various double-staining methods (Kawamura, A., Jr., Fluorescent Antibody Techniques and Their Application, Univ. Tokyo Press, Baltimore, 1977).

Many reactive fluorescent labels are available commercially (e.g., Molecular Probes) or can be synthesized using art-recognized techniques. In an exemplary embodiment, an antibody of the invention is labeled with an amine-reactive fluorescent agent, such as fluorescein isothiocyanate under mildly basic conditions. For other examples of antibody labeling techniques, see, Goding, *J. Immunol. Methods* 13: 215–226 (1976); and Goding, in, Monoclonal Antibodies: Principles and Practice, pp. 6–58, Academic Press, Orlando (1988).

In another preferred embodiment, the invention provides an isolated nucleic acid encoding an antibody or a portion of an antibody of the invention. In a further preferred embodiment, the antibody fragment is an $F_v$ fragment. $F_v$ fragments of antibodies are heterodimers of antibody $V_H$ (variable region of the heavy chain) and $V_L$ domains (variable region of the light chain). They are the smallest antibody fragments that contain all structural information necessary for specific antigen binding. $F_v$ fragments are useful for diagnostic and therapeutic applications such as imaging of tumors or targeted cancer therapy. In particular, because of their small size, $F_v$ fragments are useful in applications that require good tissue or tumor penetration, because small molecules penetrate tissues much faster than large molecules (Yokota et al., *Cancer Res.*, 52: 3402–3408 (1992)).

The heterodimers of heavy and light chain domains that occur in whole IgG, for example, are connected by a disulfide bond, but $F_v$ fragments lack this connection. Although native unstabilized $F_v$ heterodimers have been produced from unusual antibodies (Skerra et al., *Science.* 240: 1038–1041 (1988); Webber et al., *Mol. Immunol.* 4: 249–258 (1995), generally $F_v$ fragments by themselves are unstable because the $V_H$ and $V_L$ domains of the heterodimer can dissociate (Glockshuber et al. *Biochemistry* 29: 1362–1367 (1990)). This potential dissociation results in drastically reduced binding affinity and is often accompanied by aggregation.

Solutions to the stabilization problem have resulted from a combination of genetic engineering and recombinant protein expression techniques. The most common method of stabilizing $F_v$s is the covalent connection of $V_H$ and $V_L$ by a flexible peptide linker, which results in single chain $F_v$ molecules (see, Bird et al., *Science* 242: 423–426 (1988); Huston et al., *Proc. Natl. Acad. Sci. USA* 16: 5879–5883 (1988)). The single chain $F_v$s (sc$F_v$s) are generally more stable than $F_v$s alone.

Another way to generate stable recombinant $F_v$s is to connect $V_H$ and $V_L$ by an interdomain disulfide bond instead of a linker peptide; this technique results in disulfide stabilized $F_v$ (ds$F_v$). The ds$F_v$s, when they can be successfully produced, solve many problems that can be associated with sc$F_v$s: they are very stable, often show full antigen binding activity, and sometimes have better affinity than sc$F_v$s (Reiter et al., Int. *Cancer* 58: 142–149 (1994)).

Peptide linkers, such as those used in the expression of recombinant single chain antibodies, may be employed as the linkers and connectors of the invention. Peptide linkers and their use are well-known in the art. (See, e.g., Huston et al., 1988; Bird et al., 1983; U.S. Pat. No. 4,946,778; U.S. Pat. No. 5,132,405; and Stemmer et al., Biotechniques 14:256–265 (1993)). The linkers and connectors are flexible and their sequence may vary. Preferably, the linkers and connectors are long enough to span the distance between the amino acids to be joined without putting strain on the structure. For example, the linker $(gly_4ser)_3$ is a useful linker because it is flexible and without a preferred structure (Freund et al., *Biochemistry* 33: 3296–3303 (1994)).

After the stabilized immunoglobin has been designed, a gene encoding $F_v$ is constructed. Methods for isolating and preparing recombinant nucleic acids are known to those skilled in the art (see, Sambrook et al., *Molecular Cloning. A Laboratory Manual* (2d ed. 1989); Ausubel et al., *Current Protocols in Molecular Biology* (1995)).

Oligonucleotides that are not commercially available can be chemically synthesized according to the solid phase phosphoraimidite triester method first described by Beaucage & Caruthers, *Tetrahedron Letts.* 22: 1859–1862 (1981), using an automated synthesizer, as described in Van Devanter et. al., *Nucleic Acids Res.* 12: 6159–6168 (1984). Purification of oligonucieotides is by either native acrylamide gel electrophoresis or by anion-exchange HPLC as described in Pearson & Reanier, *J. Chrom.* 255: 137–149 (1983).

The sequence of the cloned genes and synthetic oligonucleotides can be verified after cloning using, e.g., the chain termination method for sequencing double-stranded templates of Wallace et al., *Gene* 16: 21–26 (1981).

One preferred method for obtaining specific nucleic acid sequences combines the use of synthetic oligonucleotide primers with polymerase extension or ligation on a mRNA or DNA template. Such a method, e.g., RT, PCR, or LCR, amplifies the desired nucleotide sequence, which is often known (see, U.S. Pat. Nos. 4,683,195 and 4,683,202). Restriction endonuclease sites can be incorporated into the primers. Amplified polynucleotides are purified and ligated into an appropriate vector. Alterations in the natural gene sequence can be introduced by techniques such as in vitro mutagenesis and PCR using primers that have been designed to incorporate appropriate mutations.

A particularly preferred method of constructing the immunoglobulin is by overlap extension PCR. In this technique, individual fragments are first generated by PCR using primers that are complementary to the immunoglobulin sequences of choice. These sequences are then joined in a specific order using a second set of primers that are complementary to "overlap" sequences in the first set of primers, thus linking the fragments in a specified order. Other suitable $F_v$ fragments can be identified by those skilled in the art.

The immunoglobulin, e.g., $F_v$, is inserted into an "expression vector," "cloning vector," or "vector." Expression vectors can replicate autonomously, or they can replicate by being inserted into the genome of the host cell. Often, it is desirable for a vector to be usable in more than one host cell, e.g., in *E. coli* for cloning and construction, and in a mammalian cell for expression. Additional elements of the vector can include, for example, selectable markers, e.g., tetracycline resistance or hygromycin resistance, which permit detection and/or selection of those cells transformed with the desired polynucleotide sequences (see, e.g., U.S. Pat. No. 4,704,362). The particular vector used to transport the genetic information into the cell is also not particularly critical. Any suitable vector used for expression of recombinant proteins host cells can be used.

Expression vectors typically have an expression cassette that contains all the elements required for the expression of the polynucleotide of choice in a host cell. A typical expression cassette contains a promoter operably linked to the polynucleotide sequence of choice. The promoter used to direct expression of the nucleic acid depends on the particular application, for example, the promoter may be a prokaryotic or eukaryotic promoter depending on the host cell of choice. The promoter is preferably positioned about the same distance from the heterologous transcription start site as it is from the transcription start site in its natural setting. As is known in the art, however, some variation in this distance can be accommodated without loss of promoter function.

Promoters include any promoter suitable for driving the expression of a heterologous gene in a host cell, including those typically used in standard expression cassettes. In addition to the promoter, the recombinant protein gene will be operably linked to appropriate expression control sequences for each host. For *E. coli* this includes a promoter such as the T7, trp, tac, lac or lambda promoters, a ribosome binding site, and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences. In one embodiment of the invention, described in Example 1, the permutated anti-Tac $F_v$ gene is operably linked to the T7 promoter. The T7 promoter is active in Studier's *E. coli* B121/ȳDE3 expression system (Studier & Moffatt, *J. Mol. Biol.* 189:113–130 (1996)).

The vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Proteins of the invention can be expressed in a variety of host cells, including *E. coli*, other bacterial hosts, yeast, and various higher eukaryotic cells such as the COS, CHO, and HeLa cells lines and mycloma cell lines. Methods for refolding single chain polypeptides expressed in bacteria such as *E. coli* have been described and are well-known and are applicable to the polypeptides of this invention. (See, e.g., Buchner et al., *Analytical Biochemistry* 205: 263–270 (1992); Pluckthun, *Biotechnology,* 9: 545 (1991); Huse, et al., *Science* 246: 1275 (1989) and Ward et al., *Nature* 341: 544 (1989)).

Often, functional protein from *E. coli* or other bacteria is generated from inclusion bodies and requires the solubilization of the protein using strong denaturants, and subsequent refolding. In the solubilization step, a reducing agent must be present to dissolve disulfide bonds as is well-known in the art. Renaturation to an appropriate folded form is typically accomplished by dilution (e.g. 100-fold) of the denatured and reduced protein into refolding buffer.

Once expressed, the recombinant proteins can be purified according to standard procedures of the art, including ammonium sulfate precipitation, affinity columns, column chromatography, and the like (see. generally, Scopes. Protein Purification (1982)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically and diagnostically.

Targeted Bioactive Agents

In another preferred embodiment, the antibodies and RAA of the invention further include a biologically active agent, preferably an antibiotic. Methods similar to those discussed above in the context of fluorescent labels can be used to attach various antibiotics to an antibody of the invention. An array of methods for attaching biologically active agents, such as antibiotics, to an antibody are available to those of skill in the art. Exemplary antibiotic compounds for conjugation to an antibody or RAA of the invention are set forth in Table 2

Table 2

Penicillins[1]

penicillin G, amoxicillin, nafcillin ampicillin, ticarcillin, negative carbenicillin, cloxacillin, penicillin V, piperacillin Cephalosporins[2]

cefoxitin, ceforanide polymyxin polymyxin B, colistin, cefepime, 3-thiaol-4-yl-carba-1-dethiacephalosporin Vancomycin[3]

daptomycin, vancomycin teicoplanin, ristocetin

Biosurfactants[4]

circulin, EM49, polypeptin, brecistin, cerexin, tridecephin, surfactin, subsporin, mycosubtilisin, bacillomycin Miscellaneous Antibiotics[5]

capreomycin, bacitracin, gramicidin, gramricidin S, tyrocidine, tazobactam, imipenem, piperacillin-tazobactam, ciprofloxacin, ceftriaxone, ceftazidime Amantadine[6]

Polyene macrolide[7]

amphotericin

Endotoxin binding tachyplesin[8]

LPS-binding antiendotoxin factor[9] LPS binding protein LPS-binding anti-endotoxin (human)[10]

[1] Mandell et al., in Goodman and Gilman's: The Pharmacological Basis of Therapeutics, 8th Ed, (Gilman, Rall, Nies, and Taylor, eds.), Pergamon Press, New York, pp. 1065–1097 (1990). [2] Id. [3] Sande et al., in Goodman and Gilman's: The Pharmacological Basis of Therapeutics, 8th Ed., (Gilman, Rall, Nies, and Taylor, eds.), Pergamon Press, New York, pp. 1117–1145 (1990). [4] Fiechter, *Trends in Biotech* 10: 208–217 (1992). [5] Mandell et al., in Goodman and Gilman's: The Pharmacological Basis of Therapeutics, 8th Ed., (Gilman, Rail, Nies, and Taylor, eds.). Pergamon Press, New York, pp. 1146–1164 (1990). [6] Douglas in Goodman and Gilman's: The Pharmacological Basis of Therapeutics, 8th Ed., (Gilman, Rail, Nies, and Taylor, eds.), Pergamon Press, New York. pp. 1182–1201 (1990). [7] Bennett in Goodman and Gilman's: The Pharmacological Basis o Therapeutics, 8th Ed., (Gilman, Rail, Nies, and Taylor, eds.), Pergamon Press, New York, pp. 1165–1181 (1990). [8] Nakamura et al., *J. Biol. Chem.* 263: 16709–16713 (1988). [9] Alpert et al., *J. Infect. Dis.* 165: 494–500 (1992). [10] Schumann et al., *Science* 249: 1429–1431 (1990). [11] Marra et al., *J. Immunol.* 148: 532–537 (1992).

Numerous agents have been developed for the cross-linking of biological molecules (see, for example, Pierce Chemical Co., (Rockford, Ill.), General Catalog, pp. E-10-E-39 (1992)). In general, cross-linking agents possess functional groups that are reactive with the side chains of different amino acids found in proteins or peptides. Various functional groups will react with primary amino groups, carboxyl groups, hydroxyl groups, or thiol groups of proteins (e.g., antibodies) or other compounds (e.g., RAA). In the design of antibody- or RAA-antibiotic conjugates, the reactive groups of both of the components must be considered. In general, antibodies have many reactive groups that can be used in direct conjugation schemes (amino acids containing primary amine, carboxyl, hydroxyl, thiol (after reduction)) or modified groups (glycosylated amino acids that can be oxidized to aldehyde; or primary amines that can be made thiol-reactive) for conjugation schemes. Similarly, the RAA of the invention can be prepared with carefully selected reactive functional groups. The selection of an antibiotic from a family of related compounds and the selection of a cross-linking scheme must also take into consideration the reactive groups on an antibiotic. Methods of forming antibody conjugates are well known in the art (see, for example, Shikhani et al. U.S. Pat. No. 5,998,381).

In an exemplary embodiment, the antibiotic attached to the antibody or RAA is an aminoglycoside. Aminoglycosides are all potent bactericidal agents that share the same general range of antibacterial activity and pharmacokinetic behavior. The members of the group are typified by the presence of aminosugars glycosidically linked to aminocyclitols. The main agents fall into two groups: the small group consisting of streptomycin, and its close relatives; and the large group which is subdivided into the neomycin group, the kanamycin group which is again subdivided into the kanamycins, tobramnycin and their semi-synthetic derivatives amikacin and dibekacin and the important sub-group of gentamicins and their relatives, netilmicin and sissomicin.

Each of the aminoglycosides has a amino group that can be derivatized to tether the antibiotic to an antibody or RAA. For example, the amine group of an amino glycoside can be converted to a carboxyl group by reacting the antibiotic with an anhydride, such as succinic anhydride. The succinyl antibiotic is isolated and purified, if desired. The free carboxyl group of the succinyl moiety is then reacted with an amine on the antibody or RAA, typically in the presence of a water-soluble dehydrating reagent, such as 1(3-dimethylaminopropyl)-3-ethylcarbodiiinide hydrochloride EDCI (Aldrich), to form an amide linkage between the carboxyl group and the antibody amine.

In another exemplary embodiment, the linker between the antibody or RAA and the antibiotic includes a cleavable moiety, such as the cis-aconityl group. The cis-aconityl group is derived from cis-aconitic anhydride (Aldrich) and the antibody-antibiotic conjugate is assembled substantially as described above for the succinyl derivative (Shen et al., Biochem. *Biophys. Res. Commun.* 102 1048 (1981), The cis-aconityl moiety is stable at neutral pH, but rapidly cleaves at a pH below about 4.5, such as might be found in an endocytotic vacuole.

Many other combinations of bioactive agents, linker moieties and methods of attaching the bioactive agent to the antibiotic will be apparent to those of skill in the art. The above discussion is intended to be illustrative of the invention and it should not be interpreted as limiting the scope of the invention or the claims as set forth herein Pharmaceutical Formulations In another preferred embodiment, the present invention provides a pharmaceutical formulation comprising the immunogenic conjugate including the target structure according to Formula IX and a pharmaceutically acceptable carrier.

In a still further preferred embodiment, the invention provides a pharmaceutical formulation including a pharmaceutically acceptable carrier and a conjugate of a bioactive agent with an antibody or RAA of the invention.

The compounds described herein, or pharmaceutically acceptable addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to patients suffering from a disease state caused by an organism that relies on an autoinducer, the compounds of the invention can be administered in cocktails containing agents used to treat the pain, infection and other symptoms and side effects commonly associated with the disease. Such agents include, e.g., analgesics, antibiotics, etc.

When administered to a patient undergoing cancer treatment, the compounds may be administered in cocktails containing anti-cancer agents and/or supplementary potentiating agents. The compounds may also be administered in cocktails containing agents that treat the side-effects of radiation therapy, such as anti-emetics, radiation protectants, etc.

Supplementary potentiating agents that can be co-administered with the compounds of the invention include, e.g., tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., setraline, trazodone and citalopram); $Ca^{+2}$ antagonists (e.g., veraparmil, nifedipine, nitrendipine and caroverine); amphotericin; triparanol analogues (e.g., tamoxifen); anti-arrhythinic drugs (e.g., quinidine), antihypertensive drugs (e.g., reserpine); thiol depleters (e.g., buthionine and sulfoximine); and calcium leucovorin.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxyniethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection. e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Vaccines

In another preferred embodiment, the present invention provides a vaccine effective for preventing or reducing microbial infection in a subject to whom the vaccine is administered. The vaccine will preferably include the immunogenic conjugate, including the target region according to Formula IX, although unconjugated autoinducers and autoinducer analogues are also useful in this embodiment. The vaccines of the invention can produce a humoral response, a cellular response or a combination of these two responses.

The vaccines of the present invention are preferably epitope-based vaccines, wherein at least a portion of the molecular structure of an autoinducer or autoinducer analogue serves as the epitope, or antigenic determinant. In the interest of clarity, the discussion below focuses on the use of an autoinducer. It is to be understood that the term autoinducer also encompasses autoinducer analogues, immunogenic conjugates of autoinducers and combinations of these compositions.

Evidence has demonstrated the value of an epitope approach to disease treatment. More specifically, vaccination, with either dominant or sub dominant epitopes has been shown to be useful in combating parasitic, microbial infections (Le et al., *Vaccine* 16: 305 (1998); Wang et al. *J. Immunol.* 157:4061 (1996); and Franke et al., *J. Immunol.* 159:424, (1997). Other studies have demonstrated that epitope vaccines are protective against acute or chronic viral infection in systems such as influenza or LCMV infection (Oukka et al., *J. Immunol.* 157: 3039 (1996); Tourdot et al., *J, Immunol.* 159: 2391 (1997); van der Most et al., *J. Immunol.* 157: 5543 (1996); van der Most et al., *J. Virol.* 71: 5110 (1997); An et al., *J. Virol.* 71: 2292 (1997)).

Furthermore, a variety of assays to detect and quantify the affinity of interaction between an epitope and MHC have also been established (Sette et al., *Curr. Opin. Immunol.* 4: 79 (1992); Sinigaglia et al., *Curr. Biol.* 6: 52 (1994); Engelhard, *Curr. Opin. Immunol.* 6: 13 (1994). Finally, a threshold of affinity associated with generation of an immune response has also been elucidated (Schaeffer et al., *Proc. Natl. Acad. Sci. USA* 86:4649(1989). Thus, by a combination of motif searches and MHC-epitope binding assays, potential candidates for epitope-based vaccines can be identified.

Various strategies can be utilized to evaluate immunogenicity and to identify immunogenic epitopes, including:

1) Evaluation of primary T cell cultures from normal individuals (see, e.g., Wentworth et al., *Mol. Immunol.* 32: 603 (1995); Celis et al., *Proc. Natl. Acad. Sci. USA* 91: 2105 (1994); Tsai et al., *J. Immunol.* 158: 1796 (1997); Kawashima et al., *Human Immunol.* 59: 1 (1998)) The procedure typically involves the stimulation of peripheral blood lymphocytes (PBL) from normal subjects with a test autoinducer in the presence of antigen presenting cells in vitro over a period of several weeks. T cells specific for the autoinducer become activated during this time and are detected using, e.g., a $^{51}$Cr-release assay involving autoinducer-sensitized target cells.

2) Immunization of HLA transgenic mice (see, e.g., Wentworth et al., *J. Immunol.* 26: 97 (1996); Wentwoth et al., *Int. Immunol.* 8: 651 (1996); Alexander et al., *J. Immunol.* 159: 4753 (1997)). In this method, autoinducer in incomplete Freund's adjuvant is administered subcutaneously to HLA transgenic mice. Several weeks following immunization, splenocytes are removed and cultured in vitro in the presence of test autoinducer for approximately one week. Autoinducer-specific T cells are detected using, e.g., a $^{51}$Cr-release assay involving autoinducer sensitized target cells and target cells expressing endogenously generated antigen.

3) Demonstration of recall T cell responses from patients who have been effectively vaccinated or who have a tumor; (see, e.g., Rehermann et al., *J. Exp. Med.* 181: 1047 (1995); Doolan et al., *Immunity* 7: 97 (1997); Bertoni et. al., *J. Clin. Invest.* 100: 503 (1997); Threlkeld et al., *J. Immunol.* 159: 1648 (1997); Diepolder et al., *J. Virol.* 71: 6011 (1997); Tsang et al., *J. Natl. Cancer Inst.* 87: 982 (1995); Disis et al., *J. Immunol.* 156: 3151 (1996)). In applying this strategy, recall responses are detected by culturing PBL from patients with a disease who have generated an immune response "naturally", or from patients who were vaccinated with autoinducer antigen vaccines. PBL from subjects are cultured in vitro for 1–2 weeks in the presence of test autoinducer plus antigen presenting cells (APC) to allow activation of "memory" T cells, as compared to "naive" T cells. At the end of the culture period, T cell activity is detected using assays for T cell activity including $^{51}$Cr release involving autoinducer-sensitized targets, T cell proliferation, or lymphokine release.

Conventional assays utilized to detect T cell responses include proliferation assays, lymphokine secretion assays, direct cytotoxicity assays, and limiting dilution assays. For example, antigen-presenting cells that have bun incubated with a peptide can be assayed for the ability to induce CTL responses in responder cell populations. Antigen-presenting cells can be normal cells such as peripheral blood mononuclear cells or dendritic cells. Alternatively, mutant non-human mammalian cell lines that are deficient in their ability to load class I molecules with internally processed peptides and that have been transfected with the appropriate human class I gene, may be used to test for the capacity of the peptide to induce in vitro primary CTL responses.

Peripheral blood mononuclear cells (PBMCs) may be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells.

More recently, a method has been devised which allows direct quantification of antigen-specific T cells by staining with fluorescein-labeled HLA tetrameric complexes (Altman et al., *Proc. Natl. Acad. Sci. USA* 90: 10330 (1993); Altman et al., *Science* 274: 94 (1996)). Other relatively recent technical developments include staining for intracellular lymphokines, and interferon-γ release assays or ELISPOT assays. Tetramer staining, intracellular lymphokine staining and ELISPOT assays all appear to be at least 10-fold more sensitive than more conventional assays (Lalvani et al. *J. Exp. Med.* 186: 859 (1997); Dunbar et al., *Curr. Biol.* 8: 413 (1998); Murali-Krishna et al., *Immunity* 8: 177 (1998)).

Once appropriately immunogenic epitopes have been defined, they can be sorted and delivered by various means, including lipopeptides (Vitiello et al., *J. Clin. Invest.* 95: 341 (1995)), viral delivery vectors (Perkus et al., in, Concepts in Vaccine Development, Kaufmann (ed.), p. 379, 1996; Chakrabarti et al., *Nature* 320: 535 (1986); Hu et al., *Nature* 320: 537 (1986); Kieny et al., *AIDS Bio/Technology* 4: 790 (1986); Top et al., *J. Infect. Dis.* 124: 148 (1971); Chanda et al., *Virology* 175:535 (1990)), particles of viral or synthetic origin (Kofler et al., *J. Immunol. Methods.* 192: 25 (1996); Eldridge et al., *Sem. Hematol.* 30: 16 (1993); Falo et al., *Nature Med.* 7: 649 (1995)), adjuvants (Warren et al., *Annu. Rev. Immunol.* 4: 369 (1986); Gupta et al., *Vaccine* 11: 293 (1993)) and liposomes (Reddy et al., *J. Immunol.* 148:1585 (1992); Rock, *Immunol. Today* 17: 131 (1996)).

Immunogenic compositions suitable for use as vaccines may be prepared from immunogenic conjugates as disclosed herein. The immunogenic conjugate elicits an immune response, which produces antibodies that bind to autoinducers, thereby inactivating them.

Vaccines may be prepared as injectables, as liquid solutions or emulsions. The peptides may be mixed with pharmaceutically-acceptable excipients, which are compatible with the peptides. Excipients may include water, saline, dextrose, glycerol, ethanol, and combinations thereof. The vaccine may further contain auxiliary substances such as wetting or emulsifying agents, pH buffering agents, or adjuvants to enhance the effectiveness of the vaccines.

The immunogens of this invention may be combined or mixed with various solutions and other compounds as is known in the art. For example, an immunogen may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella perlussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use. The discussion above concerning pharmaceutical formulations is also relevant to the formulation of the vaccines of the invention.

Preferably, the vaccines are formulated to contain a final concentration of immunogen in the range of from 0.2 to 200 µg/ml, preferably 5 to 50 µg/ml, most preferably 15 µg/ml. After formulation, the vaccine may be incorporated into a sterile container, which is then sealed and stored at a low temperature, for example 4° C., or it may be freeze-dried. Lyophilization permits long-term storage in a stabilized form.

Administration

The vaccines may be administered by any conventional methods including oral administration and parenteral (e.g., subcutaneous or intramuscular) injection. The treatment can consist of a single dose of vaccine or a plurality of doses over a period of time. The immunogen of the invention can be combined with appropriate doses of compounds including other epitopes of the target bacteria. Also, the immunogen can be a component of a recombinant vaccine, which could be adaptable for oral administration.

The recipient of the vaccine is preferably a mammal. Although use in humans in preferred, veterinary use of the compositions of the invention is also contemplated The proportion of immunogen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the immunogen can range from about 5 µg to about 100 µg of immunogen per patient of about 70 kg. A preferably range is from about 20 µg to about 40 µg per dose. A suitable dose size is about 0.5 ml. Accordingly, a dose for intramuscular injection, for example, would comprise 0.5 ml containing 20 µg of immunogen in admixture with 0.5% aluminum hydroxide.

Vaccines of the invention may be combined with other vaccines for other diseases to produce multivalent vaccines. A pharmaceutically effective amount of the immunogen can be employed with a pharmaceutically acceptable carrier such as a protein or diluent useful for the vaccination of mammals, particularly humans. Other vaccines may be prepared according to methods well-known to those skilled in the art.

The vaccines of the present invention may also be administered in conjunction with immune stimulating complexes (ISCOMs). ISCOMs are negatively charged cagelike structure of 30–40 nm in size formed spontaneously on mixing cholesterol and Quil A (saponin). Protective immunity has been generated in a variety of experimental models of infection including toxoplasmosis and Epstein-Barr virus-induced tumors using ISCOMs as the delivery vehicle for antigens (see, e.g., Mowat et al., *Immunol. Today,* 23: 383–385 (1991)). Immunogenic compositions using ISCOMs are comprised of a compound or composition of the invention encapsulated into ISCOMs for delivery.

Immunotherapy regimens which produce maximal immune responses following the administration of the fewest number of doses, ideally only one dose, are highly desirable. This result can be approached through entrapment of immunogen in macromolecular vehicles, such as microparticles, liposomes and the like. For example, the absorbable suture material poly(lactide-co-glycolide) co-polymer can be fashioned into microparticles containing immunogen (see, e.g. Eldridge et al., *Molec. Immunol.,* 28: 287–294 (1991); Moore et al., *Vaccine* 13: 1741–1749 (1995); and Men et al., *Vaccine,* 13: 683–689 (1995)). Following oral or parenteral administration, microparticle hydrolysis in vivo produces the non-toxic byproducts, lactic and glycolic acids, and releases immunogen largely unaltered by the entrapment process. Microparticle formulations can also provide primary and subsequent booster immunizations in a single administration by mixing immunogen entrapped microparticles with different release rates. Single dose formulations capable of releasing antigen ranging from less than one week to greater than six months can be readily achieved.

The immunogens of the invention may also be administered via liposomes, which serve to target the immunogens to a particular tissue, such as lymphoid tissue, or targeted selectively to infected cells, as well as increase the half-life of the immunogen composition. Liposomes include emulsions, foams, micelles, insoluble monolayers, liquid crystals, phospholipid dispersions lamellar layers and the like. In these preparations the immunogen to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes either filled or decorated with a desired immunogen of the invention can be directed to the site of lymphoid cells, where the liposomes then deliver the immunogen compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g. Szoka, et al. *Ann. Rev. Biophys. Bioeng.,* 9: 467 (1980), and U.S. Pat. Nos. 4,235,871; 4,501,728; 4,837,028; and 5,019,369.

Libraries

Also within the scope of the present invention are libraries of the autoinducer analogues, immunogenic conjugates and antibodies of the invention. The libraries will preferably include at least 10 compounds, more preferably at least 100 compound, even more preferably at least 1000 compounds and still more preferably at least 100,000 compounds.

Parallel, or combinatorial, synthesis has as its primary objective the generation of a library of diverse molecules which all share a common feature, referred to throughout this description as a scaffold. By substituting different moieties at each of the variable parts of the scaffold molecule, the amount of space explorable in a library grows. Theories and modem medicinal chemistry advocate the concept of occupied space as a key factor in determining the efficacy of a given compound against a given biological target. By creating a diverse library of molecules, which explores a large percentage of the targeted space, the odds of developing a highly efficacious lead compound increase dramatically.

Parallel synthesis is generally conducted on a solid phase support, such as a polymeric resin. The scaffold, or other suitable intermediate is cleavably tethered to the resin by a chemical linker. Reactions are carried out to modify the scaffold while tethered to the particle. Variations in reagents and/or reaction conditions produce the structural diversity, which is the hallmark of each library.

Parallel synthesis of "small" molecules (non-oligomers with a molecular weight of 200–1000) was rarely attempted prior to 1990. See, for example, Camps. et al., *Annaks de Quimica.* 70: 848 (1990). Recently, Ellmann disclosed the solid phase-supported parallel (also referred to as "combinatorial") synthesis of eleven benzodiazepine analogs along with some prostaglandins and beta-turn mimetics. These disclosures are exemplified in U.S. Pat. No. 5,288, 514. Another relevant disclosure of parallel synthesis of small molecules may be found in U.S. Pat. No. 5,324,483. This patent discloses the parallel synthesis of between 4 and 40 compounds in each of sixteen different scaffolds. Chen et al. have also applied organic synthetic strategies to develop non-peptide libraries synthesized using multi-step processes on a polymer support (Chen et al., *J. Am. Chem. Soc.,* 116: 2661–2662 (1994)).

In an exemplary embodiment of this aspect of the invention, referring to the synthesis of compound 4, set forth above, the carboxylic acid-derived portion ("arm") of an autoinducer library is tetahered via one of the two available carboxyl groups to a solid support, such as an amine-containing resin. For a library of at least ten compounds, this step is repeated with nine more portions of resin, each time using an arm having a structure that is different from that of any of the other arms. In the simplest embodiment, in which the library includes 10 compounds, each of the pools of resin having a different arm is reacted with the same heterocyclic moiety, thereby producing a library of 10 compounds that has diversity in the structure of the arms.

In a more complex library, each of the 10 pools of resin, above, is divided into, for example, 10 subpools and each of the 10 subpools having a common arm is reacted with a different heterocyclic moiety, producing a single unique compound per subpool, 10 unique compounds per pool and a library having diversity in both the arms and the heterocycle and including 100 unique compounds. Many methods of introducing molecular structural diversity into libraries of compounds are known in the art and are appropriate for use in the present invention (see, for example, Combinatorial Chemistry and Molecular Diversity in Drug Discovery, Gordon et al. (eds.), Wiley-Liss, New York, 1998.

Once a library of unique compounds is prepared, the preparation of a library of immunoconjugates, or antibodies can be prepared using the library of autoinducers as a starting point and using the methods described herein.

Kits

In another aspect, the present invention provides kits containing one or more of the compounds or compositions of the invention and directions for using the compound or composition. In a preferred embodiment, the invention provides a kit for detecting an autoinducer in a sample. The kit includes an antibody that binds specifically to the autoinducer and directions for using the antibody to detect the autoinducer. Other formats for kits will be apparent to those of skill in the art and are within the scope of the present invention.

Methods

In addition to the compositions and constructs described above, the present invention also provides a number of methods that can be practiced utilizing the compounds and conjugates of the invention.

Purification

In another preferred embodiment, the present invention provides a method for isolating a microbial receptor, which binds to a molecule having as a portion of its structure the group according to Formula I. The method preferably comprises, contacting a microbial preparation that includes the receptor with an immobilized compound according Formula IX, thereby forming a complex between the receptor and the immobilized compound.

The method of the invention for isolating a microbial receptor will typically utilize one or more affinity chromatography techniques. Affinity chromatography enables the efficient isolation of species such as biological molecules or biopolymers by utilizing their recognition sites for certain supported chemical structures with a high degree of selectivity. The literature is replete with articles, monographs, and books on the subject of affinity chromatography, including such topics as affinity chromatography supports, crosslinking members, ligands and their preparation and use. A sampling of those references includes: Ostrove, *Methods Enzymol.* 182: 357–71 (1990); Ferment, *Bioeng.* 70: 199–209 (1990). Huang et al., *J. Chromatogr.* 492: 431–69 (1989); "Purification of enzymes by heparin-Sepharose affinity chromatography," *J. Chromatogr.,* 184: 335–45 (1980); Farooqi, *Enzyme Eng.,* 4: 441–2 (1978); Nishikawa, Chem. Technol. 5(9): 564–71 (1975); Guilford et al., in, Pract. High Perform. Liq. Chromatogr., Simpson (ed.), 193–206 (1976); Nishikawa, *Proc. Int. Workshop Technol. Protein Sep. Improv. Blood Plasma Fractionation*, Sandberg (ed.), 422–35; (1977) "Affinity chromatography of enzymes," *Affinity Chromatogr., Proc. Int. Symp.* 25–38, (1977) (Pub. 1978); and Affinity Chromatography: A Practical Approach, Dean et al. (ed.), IRL Press Limited, Oxford England (1985). Those of skill in the art will have ample guidance in developing particular affinity chromatographic methods utilizing the materials of the invention.

In the present method, affinity chromatographic media of varying chemical structures can be used as supports. For example, agarose gels and cross-linked agarose gels are useful as support materials, because their hydrophilicity makes them relatively free of nonspecific binding. Other useful supports include, for example, controlled-pore glass (CPG) beads, cellulose particles, polyacrylamide gel beads and Sephadex™ gel beads made from dextran and epichlorohydrin.

The starting point for an affinity separation is the reversible interaction between a receptor (R) and a ligand for that receptor (L) as expressed by the following equation:

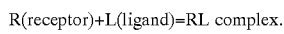

R(receptor)+L(ligand)=RL complex.

In affinity chromatography, this reaction between the receptor and the affinity matrix-bound ligand (e.g., autoinducer analogue) is used to selectively extract the receptor from crude solutions, either as a batch or continuous process. After washing away the contaminating proteins, the receptor is freed from the matrix by introducing free ligand, which competes with the matrix for binding to the receptor. The eluted receptor is freed of inhibitor by dialysis or ultrafiltration techniques, or in the case of strong binding ligands by chemical processes that interfere with binding of the ligand to the receptor.

The affinity matrix is typically packed in a cylindrical column to permit a continuous flow process, although batch operation are a reasonable alternative for extracting the enzyme from crude preparations. The affinity column can be protected by a guard column of native supporting matrix (e.g. Sepharose CL-4B) to filter out proteins that bind non specifically to the matrix and would be difficult to wash away completely from the bound receptor-ligand complex.

Both columns are typically equilibrated with a buffer at neutral pH prior to application of the receptor solution, for which 3 or more column volumes is regarded as sufficient. Any nonreactive compound with a pKa near neutrality is satisfactory. Quite often a buffer such as N-[2-hydroxyethyl] piperazine-N'-[2-ethanesulfonic acid] (HEPES) proves to be satisfactory. Other components can be included in the buffer, such as sucrose, 3-[3-cholamidopropyl)dimethylamino]-1-propanesulfonate (CHAPS) to slow the rate of dissociation of, for example, receptors having multiple subunits. Other useful buffer solutions and additives for a given purpose will be apparent to those of skill in the art.

The flow rate through the column can vary over a wide range. An important consideration in the choice of flow rates is the rate constant for association and dissociation of the receptor and the ligand. When the rates of association are slower than normal, slow flow rates are generally used (e.g., flow rate equivalent to ¼ bed volume per hour)

Following its immobilization on the affinity matrix, the bound receptor is generally washed with buffer to remove the last traces of contaminating proteins. Extensive washing, using as much as 20 column volumes of buffer, is desirable and generally leads to no detectable loss during this process.

Following the purification, it is often be desirable to remove the purified molecule (e.g. receptor) from the chromatographic matrix. Thus, in a preferred embodiment, the method of the invention further comprises disrupting the complex between the purified molecule and the molecule, thereby separating the molecule from the particle. The receptor is typically eluted from the matrix by including the free ligand, or another compound that binds the receptor in the wash buffer. Again, the rate constants for equilibration with particular ligands require special consideration. The half-life for dissociation of the ligand can be used as a guide for ascertaining appropriate flow rates. If the rates are too slow to use continuous flow to elute the receptor, elution is accomplished in a batch process, in which the column is flooded with free ligand and then incubated for a period (e.g., overnight) to allow the exchange to reach equilibrium before restarting the flow to elute the receptor.

Lastly, purified receptor can be separated from the RL complex. At this point, the purified receptor is complexed with the eluting ligand. Removal of the ligand is generally accomplished by dialysis or diafiltration. Similar methods are available for purification of other biomolecules.

In a variation on this method, the receptors can be utilized as components of the affinity matrix to isolate the components to which they bind.

Although the above discussion focuses on the purification of cellular receptors, it is within the scope of the present invention to utilize the affinity chromatographic method for the purification of any member of any class of molecules, including, for example, peptides, ligands, enzymes, enzyme substrates, carbohydrates, nucleic acids, antibodies, antigens and combinations thereof.

In a variation on the above-described method, the invention also provides a method of isolating an autoinducer. The method includes the steps of: (a) providing a sample comprising the autoinducer; (b) contacting the sample with an antibody that specifically binds to the autoinducer, thereby forming an antibody-autoinducer complex; ant (c) isolating the autoinducer by isolating the antibody-autoinducer complex. The preferred embodiments of this method are substantially similar to those discussed above, with the exception that the antibody, and not the autoinducer analogue, is preferably bound to a support.

Assays

The compositions and compounds of the invention can also be used in an array of different assay formats. In the interest of clarity, the use of the compositions and compounds in assays is illustrated by relying on immunoassays as a representative assay motif. It will be apparent to those of skill in the art that the compositions of the invention are applicable to assay formats other than immunoassays.

A variety of immunoassay formats may be used to select antibodies specifically immunoreactive with a particular autoinducer. For example, solid-phase ELISA immunoassays are routinely used to select antibodies specifically immunoreactive with a protein or other substance (see. e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

In addition to the detection of autoinducers, immunoassays can be used to qualitatively or quantitatively analyze autoinducers. A general overview of the applicable technology can be found in Harlow & Lane, supra.

Methods of producing polyclonal and monoclonal antibodies that react specifically with autoinducers are known to those of skill in the art (see. e.g., Coligan, Current Protocols in Immunology (1991); Harlow & Lane, supra; Goding, Monoclonal Antibodies: Principles and Practice (2d ed. 1986); and Kohler & Milstein, *Nature* 256: 495–497 (1975). Such techniques include antibody preparation by, for example, selection of antibodies from libraries of recombinant antibodies in phage or similar vectors, as well as preparation of polyclonal and monoclonal antibodies by immunizing rabbits or mice (see. e.g., Huse et al., *Science* 246: 1275–1281 (1989); Ward et al., *Nature* 341: 544–546 (1989)).

Once the specific antibodies against a an autoinducer are available, the autoinducer can be detected by a variety of immunoassay methods. For a review of immunological and immunoassay procedures, see Basic and *Clinical Immunology (Stites & Terr eds., $7^{th}$ ed.* 1991). Moreover, the immunoassays of the present invention can be performed in any of several configurations, which are reviewed extensively in *Enzyme Immunoassay* (Maggio, ed., 1980); and Harlow & Lane, supra.

Autoinducers can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); Basic and *Clinical Immunology* (Stites & Terr, eds., $7^{th}$ ed. 1991). Immunological binding assays (or immunoassays) typically use an antibody that specifically binds to a protein or antigen of choice (in this case an autoinducer or a substructure thereof). The antibody (e.g., anti-autoinducer) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent can be a labeled autoinducer or a labeled anti-autoinducer antibody. Alternatively, the labeling agent may be a third moiety, such as a secondary antibody, that specifically binds to the antibody/autoinducer complex (a secondary antibody is typically specific to antibodies of the species from which the first antibody is derived). Other proteins capable of specifically binding immunoglobulin constant regions, such as protein A or protein G may also be used as the labeled agent. These proteins exhibit a strong non-immunogenic reactivity with immunoglobulin constant regions from a variety of species (see, e.g., Kronval et al., *J. Immunol.* 111: 1401–1406 (1973); Akerstrom et al., *J. Immunol.* 135: 2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting or quantitating a material (e.g., an autoinducer) in samples may be either competitive or noncompetitive. Noncompetitive immunoassays are assays in which the amount of antigen is directly measured. In one preferred "sandwich" assay, for example, an anti-autoinducer antibody can be bound directly to a solid substrate on which they are immobilized. These immobilized antibodies then capture the autoinducer present in the test sample. The autoinducer is thus immobilized and then bound by a labeling agent, such as a second autoinducer antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive assay formats

In competitive assays, the presence or amount of a material (e.g., an autoinducer) present in the sample is measured indirectly by, for example, measuring the amount of a known, added (exogenous) autoinducer displaced (competed away) from an anti-autoinducer antibody by the unknown autoinducer present in a sample. In one competitive assay, a known amount of the autoinducer is added to a sample and the sample is then contacted with an antibody that specifically binds to the autoinducer. The amount of exogenous autoinducer bound to the antibody is inversely proportional to the concentration of the autoinducer present in the sample. In a particularly preferred embodiment, the antibody is immobilized on a solid substrate. The amount of autoinducer bound to the antibody may be determined either by measuring the amount of autoinducer present in a autoinducer/antibody complex, or alternatively by measuring the amount of remaining uncomplexed protein. The amount of autoinducer can be detected by providing a labeled autoinducer molecule.

A hapten inhibition assay is another preferred competitive assay. In this assay a known autoinducer is immobilized on a solid substrate. A known amount of anti-autoinducer antibody is added to the sample, and the sample is then contacted with the immobilized autoinducer. The amount of anti-autoinducer antibody bound to the known immobilized autoinducer is inversely proportional to the amount of autoinducer present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above Cross-reactivity Determinations Immunoassays in the competitive binding format can also be used for cross-reactivity determinations for a material (e.g., an autoinducer). For example, a first autoinducer can be immobilized to a solid support. Other autoinducers, are added to the assay so as to compete for binding of the antisera to the immobilized autoinducer. The ability of the added autoinducer(s) to compete for binding of the antisera to the immobilized autoinducer is compared to the ability of the first autoinducer to compete with itself. The percent cross-reactivity for the above autoinducers is calculated, using standard calculations. Those antisera with less than 10% cross-reactivity with each of the added autoinduecrs are selected and pooled. The cross-reacting antibodies are optionally removed from the pooled antisera by immunoabsorption with the added autoinducers, e.g., related structural homologs.

The immunoabsorbed and pooled antisera are then used in a competitive binding immunoassay as described above to compare a second autoinducer, thought to be substantially structurally equivalent, to the immunogen autoinducer. In order to make this comparison, the two autoinducers are each assayed at a wide range of concentrations and the amount of each autoinducer required to inhibit 50% of the binding of the antisera to the immobilized autoinducer is determined. If the amount of the second protein required to inhibit 50% of binding is less than 10 times the amount of the first autoinducer that is required to inhibit 50% of binding, then the second protein is said to specifically bind to the polyclonal antibodies generated to the respective autoinducer immunogen.

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P) enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize the autoinducer, or secondary antibodies that recognize anti-autoinducer antibodies.

The molecules can also be conjugated directly to signal generating compounds, e.g., by conjugation with an enzyme or fluorophore. Enzymes of interest as labels will primarily be hydrolases, particularly phosphatases, estesases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

In a further preferred embodiment, the instant invention provides a method of monitoring the amount of autoinducer in a patient treated with an agent that inhibits the growth of an organism producing the autoinducer. The method includes the steps of: (a) providing a sample from the patient treated with the growth inhibiting agent; (b) contacting the sample with an antibody that specifically binds to an autoinducer; and (c) determining the amount of autoinducer in the patient sample by detecting the antibody and comparing the amount of antibody detected in the patient sample to a standard curve, thereby monitoring the amount of autoinducer in the patient.

In a preferred embodiment, the method is used to optimize the dosage of the growth inhibiting agent, thus, the method further includes the step of adjusting the dose of the growth inhibiting agent administered to the patient after examining the results of the assay.

Both of the above-described embodiments of the present invention are useful in a number of methods of clinical and diagnostic relevance. Thus, in a preferred embodiment, the invention provides a method of detecting an autoinducer in a sample derived from a cultured cell, a patient sample and combinations thereof. Presently preferred patient samples are blood samples, although other samples can be examined using the methods of the invention. Human samples are also preferred and among samples from humans those derived from patients with cystic fibrosis and a microbial infection are presently preferred.

Treatment of Diseases

In another aspect, the present invention provides a method for treating or preventing a disease in a subject. The method includes administering to the subject an amount of a composition of the invention that is sufficient to treat or prevent the disease. Compositions of the invention appropriate for use in this aspect include, but are not limited to, autoinducer analogues, antibodies, immunogenic conjugates and combinations thereof. Moreover, in a preferred embodiment, the compounds of the invention are conjugated with a bioactive agent.

The compositions of the present invention are of particular use in the treatment or prevention of diseases that are associated with organisms that make use of autoinducers as a component of a quorumsensing signal mechanism. Quorum sensing is a mechanism that is used by species, such as Gram-negative bacteria to induce differentiation and biofilm development (Fuqua et al., *J. Bacteriol.* 176: 269 (1994); Fuqua et al., *Ann. Rev. Microbiol.* 50: 727 (1996)). "Biofilm," as used herein, refers to a protected mode of growth of a microorganism. The biofilm is a structured environment containing channels through which nutrients can flow. A biofilm can be formed by members of the same species, or one species can coaggregate with multiple partners. The other partners can also aggregate with other partners, leading to the formation of a dense bacterial plaque (Whittaker et al. *Annu. Rev. Microbiol.* 50: 513 (1996); DeBeer et al., *Biotech. Bioeng.* 44: 636 (1994)).

The organization of microorganisms into a biofilm has been found to be modulated by signaling molecules, such as acylhomoserine lactone produced by individual cells. At a critical cell density, the signal molecules accumulate to such a degree that they trigger the expression of specific sets of genes, which have been implicated in the formation of biofilms.

Biofilms are of interest in medicine, because the organization of a microbial colony in a host into a biofilm profoundly affects the access to much of the colony of exogenous therapeutic agents and the host immune system (Cheema et al. *J. Pharm. Pharmacol.* (suppl. 38): 53P (1986); Gordon et al., *J. Antimicrob. Chemother.* 22: 667 (1988)). Thus, a method of interfering with the quorumsensing mechanism and preventing or lessening the extent of biofilm formation, allows the microbial infection to be more effectively treated using exogenous agents and also allows components of the host immune system improved access to the members of the microbial colony.

In another preferred embodiment, the invention provides a method for preventing or disrupting the formation of a biofilm, the method comprising contacting a microbial culture capable of forming a biofilm with a composition of the invention.

In a preferred embodiment of each of the above-described embodiments of the invention, the instant method is used as a component of the treatment of a microbial infection accompanying cystic fibrosis, such as *P. aeruginosa*.

Thus, in another preferred embodiment, the method is used to disrupt or prevent formation of a biofilm associated with an implanted medical device, such as a catheter or stent (Stickler et al., *Appl. Environ. Microbiol.* 64: 3486 (1998)).

Regulation of Gene Expression

In another preferred embodiment, the present invention provides a method of controlling autoinducer responsive gene expression in a microorganism. The method includes contacting the microorganism with a compound or composition of the invention is an amount effective to control the gene expression. The control exercise can be to decrease, but is preferably used to increase, gene expression. The organisms concerned include bacteria, both Gram-positive and Gram-negative, yeast and fungi. This control technique preferably involves the use of microorganisms that are not themselves capable of producing an autoinducer, but which are capable, in the presence of an exogenous autoinducer, of expressing a gene, preferably in an easily detectable manner. The dosage of a compound of the invention necessary to affect gene expression can be ascertained by monitoring the gene expression using art recognized methods. Methods of regulating gene expression by the application of endogenous autoinducers and detecting the regulation of the gene expression are described in Bycroft et al., U.S. Pat. No. 5,593,827 and Salmond et al., U.S. Pat. No. 5,821,077, for example.

In another preferred embodiment, gene expression is decreased by contacting the microorganism with an antibody of the invention in an amount effective to control said gene expression.

The materials and methods of the present invention are further illustrated by the examples, which follow. These examples are offered to illustrate, but not to limit the claimed invention.

EXAMPLES

The following Examples describe the synthesis and characterization of two of the reactive autoinducer analogues of the invention. Example 1 sets for the synthesis of 6-{N-((3S)-2-oxo(3,3,4,5-trihydrofuryl))-carbamoyl}-hexanoic acid (4). Example 2 sets forth the synthesis of 13-{N-((3S)-2-oxo(3,3,4,5-trihydrofuryl))-carbamoyl}-11-oxoxtridecanoic acid (13).

Example 1

The following example sets forth the synthesis and characterization of Compound 4.

1.1 Cyclization of adipic acid to Produce Compound 1

Adipic acid (100 g, 0.68 moles) and acetic anhydride (400 mL) were combined and refluxed for 14 hours. The mixture was concentrated to an amber oil on a rotary evaporator. The product was isolated by vacuum distillation of the amber oil using an approximately 3 inch Vigreaux column. Two fractions were collected. Fraction 1 was collected between 110–125° C. and contained 36.8 g of material. Fraction 2 was collected between 125–140 C. and contained 12.2 g.

The extracts were combined to produce a nominally pure material (49 g, 56%).

1.2 Acylation of benzyl Alcohol with Compound 1

Anhydride 1 (49.05 g, 0.38 moles) was added to a solution of benzyl alcohol (41.4 g, 0.38 moles) in dichloromethane (380 mL). No temperature change was noted during the addition. The mixture was stirred at room temperature, refluxed for 2 hours and then returned to room temperature, where it was maintained overnight. Compound 2 was isolated by distillation on a Kugelrohr apparatus. The fraction coming over at 160–175° C. at 0.1 mm was collected (45.1 g, 50%). 1.3 Acylation of homoserine lactone with Compound 2

Under a $N_2$ atmosphere, L-homoserine lactone hydrobromide (10 g, 55 mmol), mono-benzyladipate (2), pyridine (50 mL) and EDC hydrochloride (11.5 g, 60 mmol) were combined in dichloromethane (100 mL) in a 500 mL round-bottomed flask with cooling (~0° C.). The resulting mixture was stirred for 18 hours. The mixture was cooled to ~0° C. and ice cold 15% citric acid solution was added. The citric acid layer was separated and extracted with dichloromethane (1×100 mL). The extract was combined with the remaining dichloromethane reaction solution and the combined dichloromethane solutions were washed with brine, dried over sodium sulfate, filtered and concentrated in vacuum, yielding 17.4 g (98.8%) of the crude product, which was slurried in isopropyl acetate to produce an off-white solid. The solid was collected and dried under high vacuum at 30° C., to produce 8.5 g (48.3%) of the desired product.

1.4 Debenzylation of Compound 3

Compound 3 (5 g, 15.6 mmol) was suspended in ethyl acetate under a $N_2$ atmosphere. 10% Pd/C was added (5 g) and the $N_2$ atmosphere was exchanged for a $H_2$ atmosphere, maintained using a balloon of $H_2$. The resulting suspension was stirred vigorously. Because of product depositing onto the catalyst, the suspension became unstirrable after approximately 1 hour. $N_2$ was bubbled through the reaction mixture to remove the $H_2$. Using an addition funnel, methanol (250 mL) was added under $N_2$ and the resulting mixture was stirred under $N_2$ was bubbled through the reaction mixture to through cellulose to remove the catalyst. The colorless filtrate was concentrated to afford an off-white solid (3.8 g). The solid was dissolved into hot acetonitrile (50 mL), filtered through cellulose and reheated to dissolve the product. The clear solution was allowed to cool slowly. The resulting needles were collected and dried at 0.1 mm Hg affording the desired product. MP: 140–141° C. Optical rotation: $[\alpha]_D(25°\ C.)=-27.0°$ (c=1, methanol). Mass spectrum (m/z): 228 (M⁻). Elemental analysis: calculated: C, 52.40; H, 6.60; N, 6.11. Found: C, 52.51; H, 6.53; N, 6.21. $^1$H NMR (DMSO) 8.35 (d, 1H); 4.5 (m, 1H); 4.2 (m, 1H); 4.3 (m, 1H); 2.1–2.2 (m, 4H); 1.5 (m, 4H). TLC (47.5:47.5:5.0 EtOAc/hexanes/AcOH), $R_f$=0.09.

Example 2

The following example sets forth the synthesis and characterization of Compound 13.

2.1 Benzylation of Undecelinic Acid to Form Compound 4

Undecelinic acid (105.5 g, 1.05 moles) was placed in a 3-neck round bottomed flask with dimethylformamide (500 mL) and potassium carbonate (249.0 g, 1.8 moles) and was stirred overnight while in a $N_2$ atmosphere. Benzyl bromide (100 g, 0.545 moles) was then added over 1 hour after which the solution was stirred for 2 hours. TLC (1:12; isopropyl ether/hexane on $SiO_2$/glass) showed that the undecelinic acid had been consumed.

The product solution was then filtered via Celite, washed twice with water (2×300 mL) and the organic phases extracted with hexane (2×700 mL). The combined product solution was then dried with magnesium sulfate, filtered and weighed to give 177 g (61 % crude yield). $^1$H NMR showed that the product solution was benzylated undecelinic acid.

2.2 Hydroboration of Compound 5 to Form Compound 6

Compound 5 (20.0 g, 72.9 mmol) and tetrahydrofuran (50 mL) were combined in a 3-neck 250 mL round-bottomed flask under an $N_2$ atmosphere. The solution was cooled to 3° C. and 1M $BH_3$/THF complex (36.4 mL) was added dropwise over twenty minutes as the solution warmed from 3° C. to 15° C. The solution was again cooled to 3° C. and upon removal from the ice bath, stirred magnetically for three hours. TLC (1:9 ethyl acetate/hexanes; developed with potassium permanganate) showed that the starting material had been consumed.

10% Sodium hydroxide (14 mL, 1–4° C.) was added over 4 minutes, 35% hydrogen peroxide (11 mL, 3–23° C.) was added over 25 minutes and the solution was allowed to warm to 17° C. over 30 minutes. Hydrochloric acid (100 mL, 1N) was added to the solution and the solution was stirred.

The solution was poured into a separatory funnel and water (50 mL) was added. The product was extracted with hexanes (2×60 mL) and then with ethyl acetate (1×75 mL). The combined organic layers were dried with magnesium sulfate. The product was filtered and the solvents were removed under vacuum at 37° C., resulting in a clear oil. The oil was dissolved in hexanes (100 mL) and ethyl acetate (4 mL). Seed crystals were added and the solution was stirred in an ice bath for 1 hour. The product was filtered and washed with cold hexanes (20 mL). The extraction process was repeated to produce a second crop and a total of 14.46 g of product (68% yield) was recovered. $^1$H NMR of the crude material showed that the material was predominantly compound 6.

2.3 Oxidation of Compound 6 to Produce Compound 7

Compound 6 (14.27 g, 48.8 mmol) was dissolved in dimethylformamide (120 mL) in a 250 mL round-bottom flask. Pyridinium dichromate (60.59 g, 161.0 mmol) was added portion-wise into the solution and the solution was stirred magnetically overnight. TLC (1:19 sodium hydroxide/dichloromethane; developed with phenylmercuric acetate) after 17 hours showed that the starting materials had been consumed.

The mixture was poured into water (600 mL) and extracted with tert-butyl methyl ether (2×600 mL). The product solution was dried with magnesium sulfate and the solvents were removed under vacuum at 35° C. The product mixture was put on a high vacuum for 4 days to give 14.02 g (94% yield) of a lavender semi-solid. $^1$H NMR analysis confirmed that compound 7 had been produced.

2.4 Chlorination of Compound 7 to give Compound 8

Compound 7 (11.05 g, 36.1 mmol) was dissolved in toluene (120 mL) in a 500 mL round-bottomed flask. The solution was cooled to approximately 0° C. and oxalyl chloride (7.87 mL, 90.2 mmol) was added over 5 minutes. The solution was stirred for overnight and after approximately 16 hours a pink oil settled in the bottom of the flask. The pink oil was pipetted out into a small flask and discarded. After the solvents were removed from the remaining fluid under a vacuum at 40° C., a yellow oil with a small amount of solid was recovered and weighed to 12.59 g. $^1$H NMR analysis confirmed that compound 7 had formed.

2.5 Preparation of Compound 9

A 500 mL 3-neck flask was equipped with an addition funnel, air condenser, mechanical stirrer and $N_2$ line. The flask was charged with 60% sodium hydride (2.48 g, 127.6 mmol) in mineral oil, which was washed/decanted with hexanes (2×20 mL). Tetrahydrofuran (80 mL) was added to the flask. Di-tert-butyl propadioic acid (20.0 g, 92.5 mmol), which had been dissolved in tetrahydrofuran (40 mL), was added to the suspension dropwise over 1 hour. The solution was stirred for another 1.5 hours. tert-Butyl bromoacetate (11.15 g, 74.0 mmol) was suspended in tetrahydrofuran (50 mL) and then added to the flask dropwise over 50 minutes. A white precipitate formed. TLC analysis (2:8 hexanes/ether; developed with potassium permanganate) showed that starting materials had been consumed.

The product solution was poured into saturated, aqueous ammonium chloride (100 mL). Water (50 mL) and hexanes (150 mL) were added to the product solution and the flask was shaken to separate layers. The organic layer was removed. The aqueous layer was again extracted using hexanes (150 mL). The organic layers were combined, dried with sodium sulfate overnight and filtered. The solvents were removed under a vacuum at 39° C. and the product weighed to give 30.93 g of crude product.

The crude product was purified using flash $SiO_2$ chromatography under the following conditions:

| Solvent | Amount |
| --- | --- |
| petroleum ether* | 50 mL |
| 2:98 ether/petroleum ether | 6 L |
| 3:97 ether/petroleum ether | 2 L |
| 5:95 ether/petroleum ether | 2 L |
| 7:93 ether/petroleum ether | 2 L |
| 15:85 ether/petroleum ether | 1 L |

*Loading solvent

TLC in 1:20 ether/petroleum ether and developed with potassium permanganate confirmed all starting materials had been consumed. Further, $^1$H NMR analysis showed that compound 9 had formed.

2.6 Synthesis of Compound 10

A 500 mL flask was flushed with $N_2$ and charged with 60% sodium hydride in mineral oil (1.59 g). The sodium hydride was washed/decanted with hexanes (2×20 mL). Tetrahydrofuran (60 mL) was added to the flask. Compound 9 (11.92 g, 36.1 mmol) was suspended in tetrahydrofuran (65 mL) and then added to the flask dropwise over 0.5 hour. The solution was then stirred for 3 hours to afford a thin suspension. Compound 8 (11.7 g, 36.1 mmol), which had been suspended in tetrahydrofuran (65 mL), was then added to the flask over 6 minutes. After 3.5 hours. TLC (2:8 ethyl acetate/hexanes; developed with potassium permanganate) of the product solution showed only a trace of starting material compound 8.

The product solution was then poured into saturated, aqueous ammonium chloride (80 mL) and water (20 mL) was added. Hexanes (225 mL) was added, the flask was agitated to produce layers and the hexanes layer was removed. The aqueous layer was extracted with hexanes (2×200 mL). The organic layers were pooled, dried with magnesium sulfate and the solvents removed under vacuum at 42° C. to give 22.2 g of a yellow oil (99% yield). ps 2.7 Synthesis of Compound 11

Compound 10 (22.0 g, 35.5 mmol) was dissolved in toluene (210 mL) in a 500 mL round-bottomed flask. p-Toluenesulfonic acid (0.43 g, 2.41 mmol) was added to the flask and the resulting solution was heated under a $N_2$ atmosphere and allowed to reflux overnight. TLC (2:8 ethyl acetate/hexanes; developed with potassium permanganate) of the solution showed that the starting material had been consumed.

The solution was washed with an aqueous buffer (125 mL) at pH 3 and with saturated, aqueous sodium chloride (125 mL, pH=3). The aqueous phase was extracted with tert-butyl methyl ether (2×400 mL). The combined organic phase was washed with water (6×100 mL) until the pH of the water washes approached neutrality. The product solution was dried with sodium sulfate and the solvents removed under vacuum at 47° C., leaving a slurry. The product was then refluxed with hexanes (50 mL) and tert-butyl methyl ether (50 mL), air dried and cooled in an ice bath to recrystallize the product. The product was rinsed with hexanes (30 mL), air dried, and weighed to give 6.0 g of product material. $^1$H NMR of the product indicated that compound 10 had formed.

2.8 Synthesis of Compound 12

A 250 mL three-necked round-bottomed flask was charged with compound 11 (5.47 g, 15.1 mmol) to which dichloromethane (50 mL) and 3-Dimethylaminopropyl)-3-ethylcarbodiimide hydrochloride (3.04 g, 15.8 mmol) were added under a $N_2$ atmosphere. The resulting dark amber solution was stirred at room temperature for 2.5 hours. Homoserine lactone hydrobromide (2.75 g, 15.1 mmol) was mixed with Hunig's Base (2.63 mL) and dichloromethane (55 mL) and added to the reaction solution via an addition funnel and stirred overnight. TLC (1:19 sodium acid/dichloromethane, 2 drops of acetic acid) of the resulting product after 18 hours showed the starting materials had been consumed.

The solution was poured into a mixture of ice water (150 ml) and 2N hydrochloric acid (11 mL). Saturated, aqueous sodium chloride (50 mL), hexanes (50 mL) and dichloromethane (50 mL) were added to separate the layers and the aqueous phase was drawn off with dichloromethane (2×110 mL). The organic phase was washed with a saturated, aqueous sodium chloride/water mixture (1:1,3×20 mL). The product solution was dried with sodium sulfate, filtered slowly through a silica pad (232 g), eluted with 90% ethyl acetal/hexanes (500 mL) and the solvents were removed under vacuum at 41° C. and the white, solid product was weighed to 4.28 g (64% yield).

2.9 Debenzylation of Compound 12 to form compound 13

A 2L 3-necked flask was equipped with a mechanical stirrer and flushed with $N_2$. A palladium/carbon catalyst (10% 0.99 g) was added to the flask. Compound 12 was dissolved in ethanol (750 mL) and dichloromethane (30 mL), and then stirred until the solid was completely dissolved. The solution was added to the flask and hydrogen gas was bubbled through the solution via a glass frit. After 2 hours, a TLC (1:9 sodium hydroxide/dichloromethane; developed with potassium permanganate) was taken and it was determined that no starting materials remained. The solution was filtered and the solvents removed under vacuum at 40° C. Thereafter, the product was placed under a vacuum for 2 hours to provide 3.11 g (95% yield) of a white, solid product.

The product was recrystallized by dissolving 2.98 g of the product in isopropyl acetate (350 mL). The solution was suction filtered and then gently stirred at room temperature overnight. The product was filtered to remove a small amount of off-white solid The filtrate was cooled in an ice bath for 1 hour to complete the precipitation and the product isolated by filtration. The product was dried in a vacuum oven (room temperature) for 4 hours affording 1.60 g of product (54% yield). TLC (1:9 sodium hydroxide/dichloromethane; developed with potassium permanganate) gave $R_f$=0.40. $^1$H NMR showed that the recovered product was indeed compound 13.

Example 3

Example 3 sets forth the preparation of conjugates to KLA and BSA, the immunization schedule in rabbits and the results of antibody titer measurements. The N-acyl derivative formed in Example 1 was conjugated by the method of Anderson et al. *J. Am Chem Soc.* 86:1839–1844 (1964)) with slight modification. A solution of Compound 4(10 mg, 43.6 μmol) NHS (5.0 mg, 43.6 μmol) and DCC (9.0 mg, 43.6 μmol) in 0.125 mL dry dimethylformamide was stirred for four hours at room temperature. The precipitated dicyclohexylurea was filtered out and discarded. 80 μL of the filtrate was added into 20 mg KLH and the remaining 20 μL was added into 10 mg of either BSA or KLH in 1.0 mL each of 0.1 M bicarbonate buffer pH 8.25. After coupling with gentle agitation on a shaker for two hours, unconjugated 4 was separated from the conjugates by passing through Sephadex G25 equilibrated with PBS pH 7.2. The protein peak was collected and set aside for immunization and ELISA screening for the antisera.

The conjugate of 4 was injected into 3 rabbits each at monthly intervals to generate polyclonal antibodies. After 3 injections (3 months) the rabbits were bled and the antibody titer measured by ELISA.

Figure X below shows the serial dilutions of the antisera of each rabbit. The dilutions that reduces the ELISA by 50% are, respectively, >1:25,600 for rabbit R263, between 1:12,800 and 1:25,600 for R261, and between 1:12,800 and 1:25,600 for R262. Similar results were obtained with 13.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A compound having the structure:

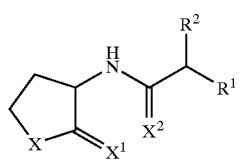

(I)

wherein, $R^1$ is a member selected from —H, —OH, and (=O);

$R^2$ is a member selected from reactive functional groups, alkyl groups terminally substituted with a reactive functional group and internally substituted alkyl groups terminally substituted with a reactive functional group wherein said alkyl groups terminally substituted with a reactive functional group and said internally substituted alkyl groups terminally substituted with a reactive functional group are substituted with a reactive functional group which is a member selected from —$OR^3$, —$NHR^4$, —$COR^5$, —SH and —$CH_2X^3$ wherein, —$OR^3$ is a member selected from hydroxy, alkyl sulfonate and aryl sulfonate groups;

$R^4$ is H;

$R^5$ is a member selected from $X^3$ and —$OR^6$, wherein $R^6$ is a member selected from alkyl, substituted alkyl, aryl, substituted aryl, heteroaryl, substituted heteroaryl, heterocyclyl and substituted heterocyclyl groups; and $X^3$ is a halogen;

X is —O—; and $X^1$ and $X^2$ are members independently selected from O and S.

2. The compound according to claim 1, wherein $R^2$ is an internally substituted alkyl group terminally substituted with a reactive functional group.

3. The compound according to claim 2, wherein the alkyl group is internally substituted with a functional group that is a member selected from —OH, (=O) and combinations thereof.

4. The compound according to claim 1, wherein the compound is a single stereoisomer.

5. The compound according to claim 1, wherein the alkyl and the internally substituted alkyl groups are members selected from $C_1$–$C_{20}$ saturated straight-chain, $C_1$–$C_{20}$ saturated branched-chain, $C_1$–$C_{20}$ unsaturated straight-chain, $C_1$–$C_{20}$ unsaturated branched-chain alkyl and internally substituted alkyl groups.

6. The compound according to claim 5, wherein the alkyl and internally substituted alkyl groups are members selected from $C_5$–$C_{10}$ saturated straight-chain, $C_5$–$C_{10}$ saturated branched-chain, $C_5$–$C_{10}$ unsaturated straight-chain, $C_5$–$C_{10}$ unsaturated branched-chain alkyl and internally substituted alkyl groups.

7. A compound according to claim 1, wherein $R^2$ has the structure:

(III)

wherein, $R^7$ a reactive functional group; and n is a number from 1 to 20, inclusive.

8. The compound according to claim 7, wherein n is a number from 2 to 9, inclusive.

9. A compound according to claim 1, wherein $R^2$ has the structure:

(IV)

wherein, $R^7$ is a reactive functional group; and q and s are numbers independently selected from 1 to 20, inclusive.

10. The compound according to claim 9, wherein s is a number from 2 to 9, inclusive.

11. A compound having the structure:

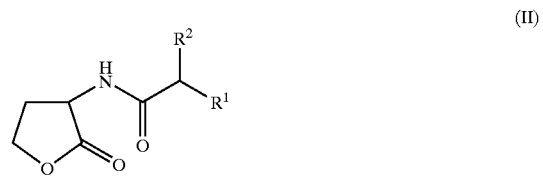

(II)

wherein, $R^1$ is a member selected from H, OH, and (=O); and $R^2$ is a member selected from H, reactive functional groups, alkyl groups terminally substituted with a reactive functional group and internally substituted alkyl groups terminally substituted with a reactive functional group, with the proviso that when $R^2$ is —OH, $R^1$ is a member selected from OH, and (=O).

12. The compound according to claim 11, wherein the reactive functional group is a member selected from —$OR^3$, —$NHR^4$, —$COR^5$, SH and $CH_2X^3$
wherein,
—$OR^3$ is a member selected from hydroxy, and a species such that —$OR^3$ is a leaving group;
$R^4$ is a member selected from H, $C_1$–$C_6$ alkyl, $C_1$–$C_6$ substituted alkyl, aryl and substituted aryl groups;
$R^5$ is a member selected from H, halogen and —$OR^6$, wherein $R^6$ is species such that —$OR^6$ is a leaving group; and
$X^3$ is a halogen.

13. The compound according to claim 12, wherein $R^3$ is

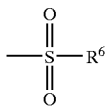 (V)

wherein,
$R^8$ is a member selected from alkyl, substituted alkyl, aryl and substituted aryl groups.

14. The compound according to claim 12, wherein $R^6$ is a member selected from alkyl, substituted alkyl, aryl, substituted aryl, heteroaryl, substituted heteroaryl, heterocyclyl and substituted heterocyclyl groups.

15. The compound according to claim 11, wherein the alkyl and the internally substituted alkyl groups are members selected from $C_1$–$C_{20}$ saturated straight-chain, $C_1$–$C_{20}$ saturated branched-chain, $C_1$–$C_{20}$ unsaturated straight-chain, $C_1$–$C_{20}$ unsaturated branched-chain alkyl and internally substituted alkyl groups.

16. The compound according to claim 15, wherein the alkyl and internally substituted alkyl groups are members selected from $C_5$–$C_{10}$ saturated straight-chain, $C_5$–$C_{10}$ saturated branched-chain, $C_5$–$C_{10}$ unsaturated straight-chain, $C_5$–$C_{10}$ unsaturated branched-chain alkyl and internally substituted alkyl groups.

17. A compound according to claim 11, wherein $R^2$ has the structure:

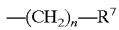 (III)

wherein,
$R^7$ is a reactive functional group; and
n is a number from 1 to 20, inclusive.

18. The compound according to claim 17, wherein n is a number from 2 to 9, inclusive.

19. The compound according to claim 11, wherein $R^2$ is a member selected from the group consisting of —COOH, —OH, —$NH_2$, and SH.

20. The compound according to claim 17, wherein $R^7$ is a member selected from the group consisting of —COOH, —OH, —$NH_2$, and —SH.

21. A compound having a structure that is a member selected from:

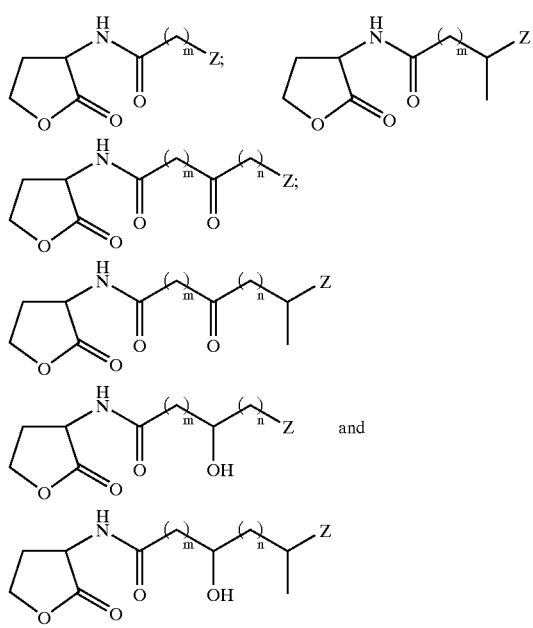

wherein,
m is a number selected from 1 to 20, inclusive;
n is a number from 0 to 20, inclusive; and
Z is a reactive functional group.

22. The compound according to claim 21, wherein m and n are numbers independently selected from 2 to 9, inclusive.

23. The compound according to claim 21, wherein Z is a member selected from —$NH_2$, —COOH, —SH, and —OH.

* * * * *

UNITED STATES PATENT AND TRADEMARK OFFICE
CERTIFICATE OF CORRECTION

PATENT NO.   : 6,703,513 B1
DATED        : March 9, 2004
INVENTOR(S)  : Steven C. Quay It is certified that error appears in the above-identified patent and that said Letters Patent is hereby corrected as shown below:

Column 49,
Beginning at line 16, kindly delete

"The compound according to claim 12, wherein $R^3$ is

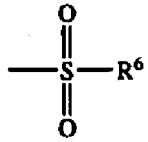

wherein, $R^8$ is a member selected from alkyl, substituted alkyl, aryl and substituted aryl groups."

and insert

-- The compound according to claim 12, wherein $R^3$ is

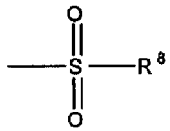

wherein, $R^8$ is a member selected from alkyl, substituted alkyl, aryl and substituted aryl groups.--

Signed and Sealed this

First Day of March, 2005

JON W. DUDAS
*Director of the United States Patent and Trademark Office*